(12) United States Patent
Tsuji et al.

(10) Patent No.: US 7,892,841 B2
(45) Date of Patent: Feb. 22, 2011

(54) METHOD AND APPARATUS FOR MEASURING HEMATOLOGICAL SAMPLE

(75) Inventors: Tomohiro Tsuji, Kobe (JP); Ayumu Yoshida, Kobe (JP); Shinichiro Oguni, Kobe (JP)

(73) Assignee: Sysmex Corporation, Hyogo (JP)

( * ) Notice: Subject to any disclaimer, the term of this patent is extended or adjusted under 35 U.S.C. 154(b) by 908 days.

(21) Appl. No.: 11/727,806

(22) Filed: Mar. 28, 2007

(65) Prior Publication Data

US 2007/0231913 A1 Oct. 4, 2007

(30) Foreign Application Priority Data

Mar. 29, 2006 (JP) ............... 2006-092480

(51) Int. Cl.
  *G01N 33/48* (2006.01)
  *G01N 21/47* (2006.01)
  *G01N 21/64* (2006.01)

(52) U.S. Cl. ............... 436/63; 436/8; 436/10; 436/164; 436/172; 436/174; 436/175; 422/73; 422/82.05; 422/82.08; 422/82.09; 435/2; 435/29

(58) Field of Classification Search ............ 436/8, 436/10, 63, 164, 166, 172, 174, 175; 422/73, 422/82.05, 82.08, 82.09; 435/2, 29
See application file for complete search history.

(56) References Cited

U.S. PATENT DOCUMENTS

| | | | | |
|---|---|---|---|---|
| 5,264,369 A | * | 11/1993 | Sakata et al. | 436/63 |
| 5,413,938 A | * | 5/1995 | Tsujino et al. | 436/63 |
| 5,538,893 A | * | 7/1996 | Sakata et al. | 436/10 |
| 5,830,701 A | * | 11/1998 | Houwen et al. | 435/29 |
| 5,905,031 A | * | 5/1999 | Kuylen et al. | 435/29 |
| 5,958,776 A | * | 9/1999 | Sakata et al. | 436/10 |
| 6,004,816 A | * | 12/1999 | Mizukami et al. | 436/10 |
| 6,900,023 B1 | * | 5/2005 | Houwen et al. | 435/7.24 |
| 7,625,712 B2 | * | 12/2009 | Paul et al. | 435/7.21 |
| 7,625,730 B2 | * | 12/2009 | Tsuji et al. | 435/173.9 |
| 7,625,757 B2 | * | 12/2009 | Tsuji et al. | 436/10 |
| 2002/0182623 A1 | | 12/2002 | Lefevre et al. | |
| 2003/0219850 A1 | * | 11/2003 | Tsuji et al. | 435/40.5 |
| 2005/0202400 A1 | | 9/2005 | Tsuji et al. | |
| 2005/0219527 A1 | | 10/2005 | Ikeuchi et al. | |
| 2007/0111276 A1 | | 5/2007 | Lefevre et al. | |
| 2008/0176274 A1 | * | 7/2008 | Tsuji et al. | 435/34 |

FOREIGN PATENT DOCUMENTS

| | | |
|---|---|---|
| EP | 1 239 283 A1 | 9/2002 |
| EP | 574 839 A1 | 9/2005 |
| WO | 2005/085842 A2 | 9/2005 |

* cited by examiner

*Primary Examiner*—Maureen M Wallenhorst
(74) *Attorney, Agent, or Firm*—Sughrue Mion, PLLC

(57) ABSTRACT

A measuring method and a measuring apparatus which can classify and count myeloblast more precisely without influence of other component in a sample including platelet aggregation in measurement of a blood sample with a flowcytometry, wherein damage is given to a cell membrane of erythrocyte and mature leukocyte contained in a hematological sample, a hemocyte in which a cell membrane is damaged is constricted, and this is dyeing-treated with a fluorescent dye which can stain a nucleic acid to obtain a sample, the sample is measured with a flowcytometer, and a cell contained in a first cell group containing myeloblast, which is specified based on forward scattered light information and side scattered light information, and contained in a second cell group containing myeloblast, which is specified based on forward scattered light information and fluorescent information, is counted as myeloblast.

20 Claims, 16 Drawing Sheets

FIG. 13
(a)
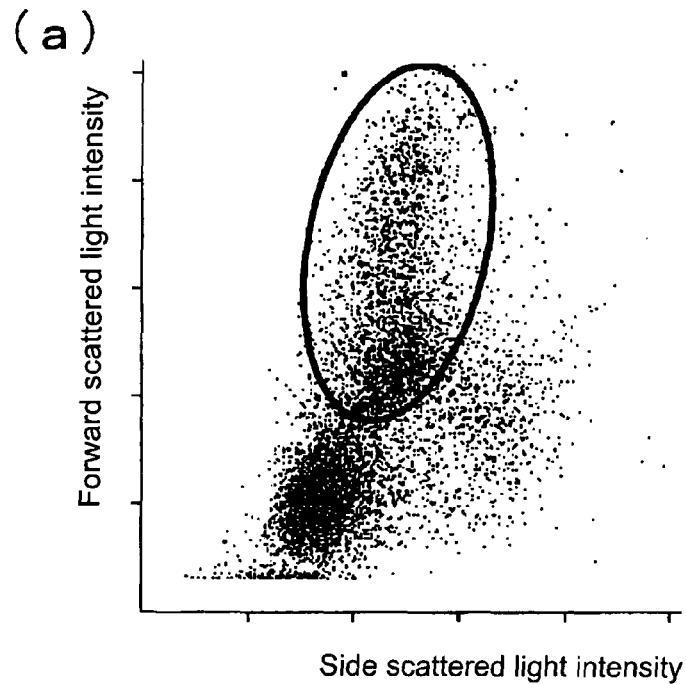
(b)
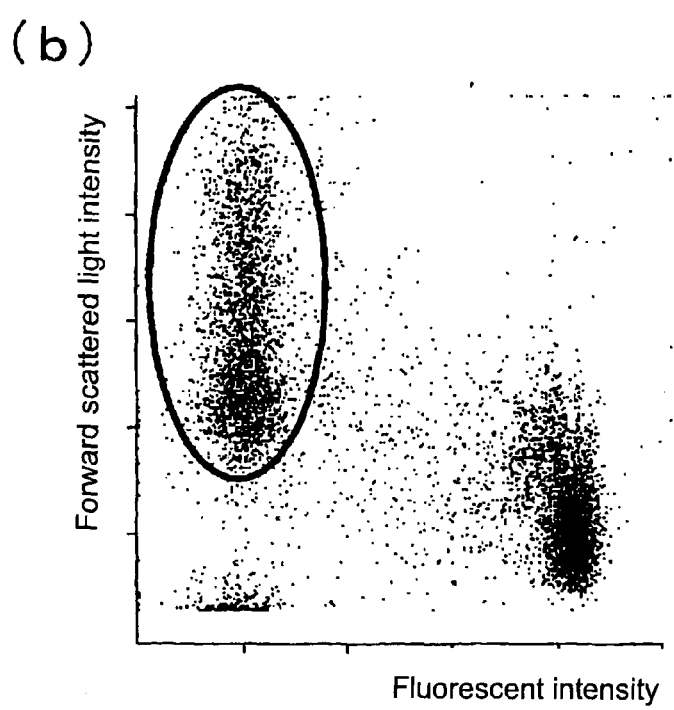

FIG. 15
(a)
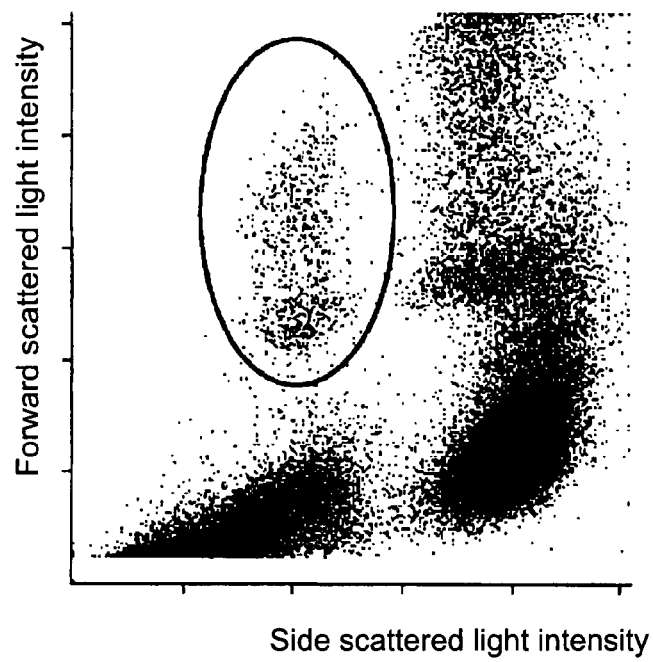
(b)
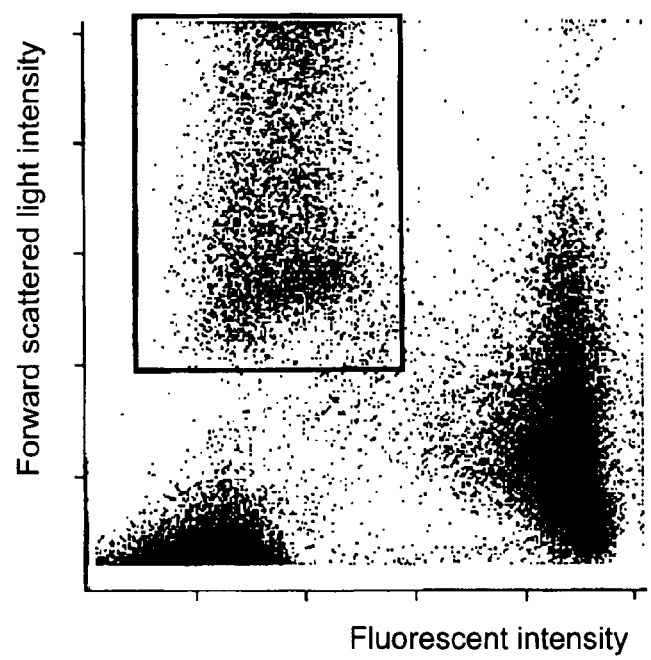

METHOD AND APPARATUS FOR MEASURING HEMATOLOGICAL SAMPLE

FIELD OF THE INVENTION

The present invention relates to a method and an apparatus for measuring a hematological sample, more particularly, a method and an apparatus for measuring a hematological sample which can count immature leukocyte, particularly, myeloblast by discriminating it from other hemocyte at a high precision.

BACKGROUND

A cell component of blood is roughly classified into platelet, leukocyte and erythrocyte and, further, leukocyte is classified into granulocyte (eosinophil, neurtrophil, and basophil), monocyte and lymphocyte. These cells are produced in bone marrow, are differentiated and matured from an immature cell, and migrated to peripheral blood. In the case of a healthy person, immature leukocyte which has not been matured to leukocyte contained in normal blood, such as granulocyte, monocyte and lymphocyte (hereinafter, these are referred to as "mature leukocyte" in some cases) does not appear in peripheral blood, but in peripheral blood of a patient with leukemia, cancer bone marrow metastasis or serious infectious disease, immature leukocyte such as myeloblast appears in some cases. Particularly, detection of myeloblast is important for diagnosing the aforementioned diseases.

As a method for automatically measuring blood collected in a clinical test or a medical examination, a measuring method utilizing flowcytometry is utilized. Flowcytometry is a method of introducing a sample obtained by fluorescently staining a cell membrane or a nucleus into a flow cell, irradiating a cell passing through a flow cell with excitation light of a dye, obtaining information regarding scattered light or fluorescent light emitted from individual cells passing through a flow cell, and measuring a kind and the number of cells from the information.

In a method for measuring a hematological sample using flowcytometry, various methods for detecting a hemocyte contained in blood, and further, immature leukocyte appearing in the case of a hemocyte disease, and a hemocyte whose form has been changed by discriminating them from other hemocyte cells are proposed.

For example, according to the technique of US2005/0202400, a hemocyte in blood is classified as in the following (1) to (3). (1) First, in a two-dimensional scattergram using a forward scattered light peak and a forward scattered light width as two axes, platelet aggregation, and leukocyte and an erythrocyte ghost are discriminated. (2) Next, leukocyte and erythrocyte ghosts discriminated in (1) are developed into a two-dimensional scattergram using a forward scattered light intensity and a fluorescent intensity as two axes, and leukocyte, and an erythrocyte ghost are discriminated. (3) Further, leukocyte discriminated in (2) is developed into a two-dimensional scattergram using a fluorescent intensity and a side scattered light intensity as two axes, and leukocyte is subclassified into lymphocyte, monocyte, granulocyte, myeloblast, and granulocyte immature-cytes.

However, according to US2005/0202400, in (3), myeloblast can be classified, but when a sample containing a small amount of platelet aggregation is measured, there is a possibility that platelet aggregation appears in a region of leukocyte and an erythrocyte ghost in (1), and appears in a region of myeloblast in (3). For this reason, development of the technique for measuring myeloblast at a better precision is desired.

SUMMARY

The scope of present invention is defined solely by the appended claims, and is not affected to any degree by the statements within this summary.

The present invention was done in view of the aforementioned circumstances, and an object thereof is to provide a measuring method an a measuring apparatus which can more precisely classify and count myeloblast without influence of other components in a sample including platelet aggregation, in measurement of a blood sample with flowcytometry.

The present inventors found out that, based on two kinds of scattered light information having different angles and fluorescent information obtained by applying a hematological sample which has been more strongly stained than immature leukocyte by giving damage to a cell membrane of mature leukocyte to flowcytometry, influence of platelet aggregation is excluded by specifying a cell group containing myeloblast based on the above two kinds of scattered light information, and myeloblast is discriminated from mature leukocyte by specifying a cell group containing myeloblast specified based on one kind of scattered light information and fluorescent information and, thereby, myeloblast can be measured, being discriminated from other hemocyte cells, which resulted in completion of the present invention.

That is, among a method for measuring a hematological sample of the present invention, the first measuring method comprises a sample treatment step of giving damage to a cell membrane of erythrocyte and mature leukocyte contained in a hematological sample, constricting a hemocyte in which a cell membrane is damaged, and dyeing this with a fluorescent dye which can stain a nucleic acid; an obtaining step of obtaining first scattered light information generated by irradiating the treated sample with light, second scattered light information based on scattered light having a different angle from that of first scattered light and fluorescent information; a first specification step of specifying a first cell group containing myeloblast based on the first scattered light information and the second scattered light information; a second specification step of specifying a second cell group containing myeloblast based on the first scattered light information and the fluorescent information; and a counting step of counting a cell belonging to both of the first and second cell groups as myeloblast.

In the counting step, a cell belonging to both of the first and second cell groups is discriminated by a scattergram using the fluorescent information and the second scattered light information as two axes, and a cell appearing in the scattergram may be counted as myeloblast.

In addition, the second specification step in the first measuring method may be a step of specifying a second cell group among the first cell group based on first scattered light information and fluorescent information of the first cell group, or the first specification step in the first measuring method may be a step of specifying the first cell group among the second cell group based on first scattered light information and second scattered light information of the second cell group (second measuring method).

In the first and second measuring methods, it is preferable that the first specification step is a step of setting a myeloblast appearance candidate region in a first scattergram using the first scatted light information and the second scattered light information as two axes, and specifying a cell group appearing in the candidate region as the first cell group, and the second specification step is a step of setting a myeloblast appearance candidate region in a second scattergram using the first scattered light information and the fluorescent information as two axes, and specifying a cell group appearing in the candidate region as the second cell group.

And, in the method for measuring a hematological sample of the present invention, the first specification step and the second specification step may be performed simultaneously. That is, the third measuring method comprises a sample treatment step of giving damage to a cell membrane of erythrocyte and mature leukocyte contained in a hematological sample, constricting a hemocyte in which a cell membrane is damaged, and dyeing this with a fluorescent dye which can stained a nucleic acid; an obtaining step of obtaining first scattered light information generated by irradiating the treated sample with excitation light of the fluorescent dye, second scattered light information based on scattered light having a different angle from that of first scattered light, and fluorescent information; a specification step of specifying a first cell group containing myeloblast based on the first scattered light information and the second scattered light information and, at the same time, specifying a second cell group containing myeloblast based on the first scattered light information and the fluorescent information; and a counting step of counting a cell belonging to both of the first and second cell groups as myeloblast.

Furthermore, a fourth measuring method of the method for measuring a hematological sample of the present invention is a method which is applied to the case where a third cell group containing total leukocyte is specified in place of a second cell group containing myeloblast, as a cell group to be specified based on the first scattered light information and the fluorescent information. That is, the fourth measuring method comprises a sample treatment step of giving damage to a cell membrane of erythrocyte and mature leukocyte contained in a hematological sample, constricting a hemocyte in which a cell membrane is damaged, and dyeing this with a fluorescent dye which can stain a nucleic acid; an obtaining step of obtaining first scattered light information generated by irradiating the treated sample with excitation light of the fluorescent coloring matter, second scattered light information based on scattered light having a different angle from that of first scattered light, and fluorescent information; a first specification step of specifying a first cell group containing myeloblast based on the first scattered light information and the second scattered light information; a third specification step of specifying a cell population other than a ghost population as a third cell group based on the first scattered light information and the fluorescent information; a fourth specification step of specifying a fourth cell group which does not substantially contain at least mature leukocyte, among the third cell group, based on second scattered light information and fluorescent information of the third cell group; and a counting step of counting a cell contained in the first cell group and contained in the fourth cell group as myeloblast.

In the method for measuring a hematological sample of the present invention, it is preferable that the first scattered light information is a forward scattered light intensity, the second scattered information is a side scattered light intensity, and the fluorescent information is a fluorescent intensity.

In addition, it is preferable that the treatment step is performed by mixing a surfactant which gives damage to a cell membrane of erythrocyte and mature leukocyte, a solubilizer which constricts a damaged hemocyte, a fluorescent dye which stains a nucleic acid, and a hematological sample.

The method for discriminating myeloblast and platelet aggregation is a method of discriminating myeloblast and platelet aggregation contained in a hematological cell, and comprises a step of giving damage to a cell membrane of erythrocyte and mature leukocyte contained in the sample, and constricting a hemocyte in which a cell membrane is damaged; a step of obtaining forward scattered light information and side scattered light information generated by irradiating the treated sample with light; and a step of discriminating the myeloblast and the platelet aggregation based on the forward scattered light information and the side scattered light information.

The apparatus for measuring a hematological sample of the present invention comprises a sample treatment part for giving damage to a cell membrane of erythrocyte and mature leukocyte contained in a hematological sample, constricting a hemocyte in which a cell membrane is damaged, and dyeing this with a fluorescent dye which can stain a nucleic acid; an obtainer for obtaining first scattered light information generated by irradiating the treated sample with excitation light of the fluorescent dye, second scattered light information based on scattered light having a different angle from that of first scattered light, and florescent information; a first classifier for specifying a first cell group containing myeloblast based on the first scattered light information and the second scattered light information; a second classifier for specifying a second cell group containing myeloblast based on the first scattered light information and the fluorescent information; and a calculator for counting a cell belonging to both of the first and second cell groups as myeloblast.

It is preferable that the first cell group is a cell group appearing in a myeloblast appearance candidate region set in a first scattergram using the first scattered light information and the second scattered light information as two axes, and the second cell group is a cell group appearing in a myeloblast appearance candidate region set in second scattergram using the first scattered light information and the fluorescent information as two axes.

It is preferable that the calculator discriminates a cell belonging to both of the first and second cell groups by a third scattergram using the fluorescent information and the second scattered light information as two axes, and counts a cell appearing in the third scattergram as myeloblast.

The measuring apparatus of the present invention may be further provided with a display part for displaying at least one of a scattergram in which a cell belonging to both of the first and second cell groups appears, and result of counting of the myeloblast, and may be further provided with a light source for irradiating the excitation light.

The "immature leukocyte" referred in the present invention refers to an immature cell which is usually present in bone marrow, and is not present in a peripheral blood liquid, such as myeloblast, promyelocyte, myelocyte, and postmyelocyte. Promyelocyte, myelocyte and postmyelocyte are collectively referred to as immature granulocyte in some cases. Furthermore, a leukocytic hematopoietic precursor cell such as marrow stem cell, neutrophil/macrophage colony forming cell, eosinophils colony forming cell and the like, which are at a differentiation stage before a blast cell, is included in the scope of immature leukocyte of the present invention.

The "mature leukocyte" referred in the present invention refers to immature lymphocyte, monocyte, granulocyte (neutrophil, eosinophils, basophil).

The "platelet aggregation" referred in the present invention refers to aggregation of two or more platelets.

The "damage of cell membrane" referred in the present invention refers to opening of such a pore in a cell membrane that a particular substance can pass therethrough.

The "hematological sample" referred in the present invention mainly refers to a peripheral blood liquid and, additionally, a sample containing a bone marrow liquid, or a blood component recovered by apheresis or the like, or a biological sample containing a leukocyte component such as an abdominal cavity liquid, a urine sample or the like is also a suitable sample.

Since the method for measuring a hematological sample of the present invention, upon discrimination of a cell group using fluorescent information and two kinds of scattered light information obtained by measuring a blood sample by flowcytometry, can specify a cell group containing myeloblast by excluding influence of platelet aggregation, the method can precisely classify and count myeloblast by appropriately combining with a particular method which can discriminate a cell group containing myeloblast and a cell group of mature leukocyte.

Since the method for measuring a hematological sample of the present invention is applied to the apparatus for measuring a hematological sample of the present invention, the apparatus can measure myeloblast at a high precision.

BRIEF DESCRIPTION OF THE DRAWINGS

FIG. 13 (*a*) is a first scattergram obtained by measuring a measuring sample prepared in Example 1, and FIG. 13 (*b*) is a second scattergram obtained by measuring the same measuring sample.

FIG. 15 (*a*) is a first scattergram obtained by measuring a measuring sample prepared in Example 1, and FIG. 15 (*b*) is a second scattergram obtained by measuring the same measuring sample.

DETAILED DESCRIPTION OF THE EMBODIMENT

Figure 1:
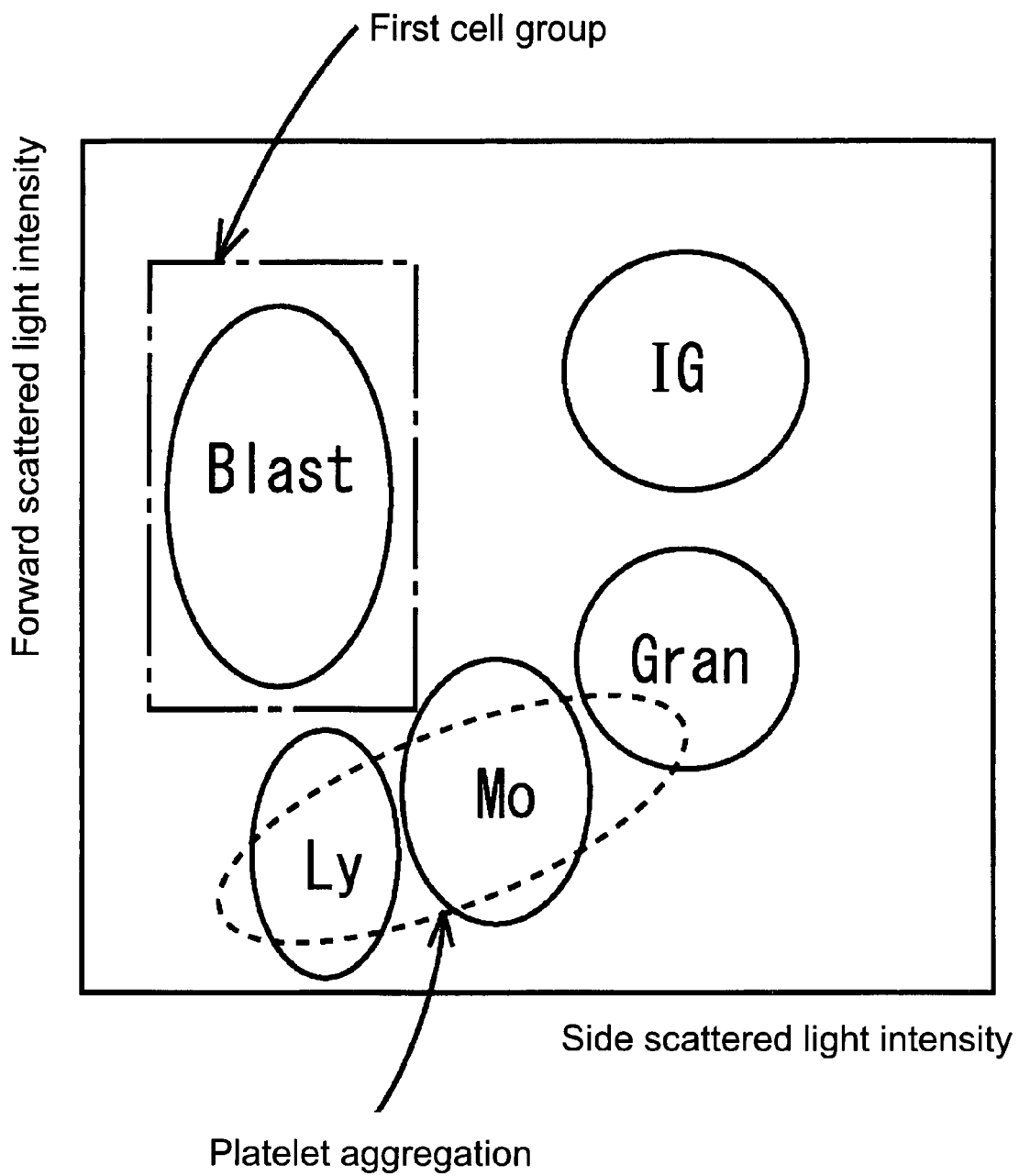
FIG. 1 is a scattergram for explaining a first cell group.

The method for measuring a hematological sample of the present invention comprises a sample treatment step of giving damage to a cell membrane of erythrocyte and mature leukocyte contained in a hematological sample, constricting a hemocyte in which a cell membrane is damaged, and dyeing this with a fluorescent dye which can stain a nucleic acid; an obtaining step of obtaining first scattered light information generated by irradiating the treated sample with excitation light of the fluorescent dye, second scattered light information based on scattered light having a different angle from that of first scattered light, and fluorescent information; a step of specifying a cell population containing myeloblast by excluding influence of platelet aggregation, and discriminating from other hemocyte cell, using the obtained fluorescent information and two kinds of scattered light information; and a counting step of counting a cell population of specified myeloblast as myeloblast.

The present invention will be specifically explained below.

[Treatment of Hematological Sample]

It is preferable that the sample treatment step in the measuring method of the present invention is performed by mixing a hematological sample and a treating reagent described below. The treating reagent is a reagent which can give damage to a cell membrane of erythrocyte and mature leukocyte contained in a hematological sample, constricting a hemocyte in which a cell membrane is damaged, and stain a nucleic acid. Specifically, the reagent includes a surfactant which gives damage to a cell membrane of erythrocyte and mature leukocyte contained in a sample, and a fluorescent dye which fluorescently stains a nucleic acid.

The surfactant used in the present invention gives damage to a cell membrane of erythrocyte and mature leukocyte. Although action of mechanism is not clear, it is thought that, by extracting (pulling out) a part of a particular cell membrane liquid constituent component, a pore through which a particular substance can pass is opened (referred to damage) in a cell membrane. And, a fluorescent dye can penetrate into the interior of a cell damaged with the surfactant, and stain a nucleic acid.

The surfactant gives damage also to immature leukocyte, but needs a time to damage a cell as compared with erythrocyte and mature leukocyte. For this reason, within a predetermined time after a hematological sample and a treating reagent are mixed, the state is realized where damaged mature leukocyte is more easily dyed than undamaged myeloblast and immature granulocyte. As a result, since myeloblast and immature granulocyte are hardly stained with a fluorescent dye which stains a nucleus as compared with mature leukocyte which undergoes damage and whose nucleus is stained, a fluorescent intensity of the myeloblast and immature granulocyte becomes lower than that of mature leukocyte.

Examples of the surfactant used in the present invention include a polyoxyethylene nonionic surfactant. Specifically, the surfactant is a nonionic surfactant represented by $R^1R^2(CH_2CH_2O)nH$. In the figure, $R^1$ is an alkyl group, an alkenyl group or an alkynyl group of a carbon number of 9 to 25, $R^2$ is —O— or —COO— or

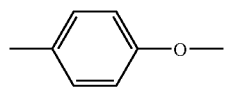

and n is an integer of 10 to 40.

Examples of the alkyl group of a carbon number of 9 to 25 include nonyl, decyl, undecyl, dodecyl, tridecyl, tetradecyl and the like. Examples of the alkenyl group of a carbon number of 9 to 25 include dodecenyl, tetradecenyl and the like. Examples of the alkynyl group of a carbon number of 9 to 25 include dodecynyl, undecynyl, dodecynyl and the like.

Specific examples include polyoxyethylene(20)lauryl ether, polyoxyethylene(15)oleyl ether, and polyoxyethylene (16)oleyl ether.

The surfactant can be used in a form of an aqueous solution. For example, a concentration of the polyoxyethylene nonionic surfactant in water is different depending on a kind of a surfactant to be used, and the polyoxyethylene(16)oleyl ether can be used in a range of 5 to 50 g/l (preferably, 15 to 35 g/l). In the polyoxyethylene nonionic surfactant, when a carbon number of a hydrophobic group is the same, as a value of n becomes smaller, a force of damaging a cell is stronger and, as a value of n becomes greater, the force is weakened. In addition, when the value of n is the same, as a carbon number of a hydrophobic group becomes smaller, a force of damaging a cell becomes stronger. In view of that point, and using the value as a measure, a required concentration of the surfactant may be appropriately obtained by an experiment.

The fluorescent dye used in the present invention is a dye which fluorescently stains a nucleic acid. For mature leukocyte in which damage is given to a cell membrane, a fluorescent dye can pass through a cell membrane, and stain a nucleus.

Specific examples include ethidium bromide, propidium iodide, and ethidium-acridine heterodimer, ethidium azide, ethidium homodimer-1, ethidium homodimer-2, ethidium monoazide, TOTO-1, TO-PRO-1, TOTO-3, TO-PRO-3, sold from Molecular Probe, and the like. Further, as a dye suitable on the case where He—Ne, or a red semiconductor laser is used as a light source, a dye represented by the following (1) formula can be used.

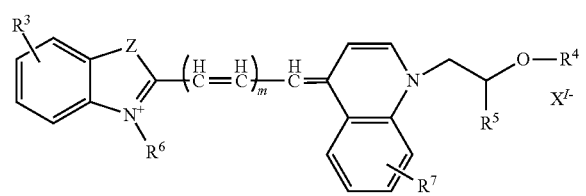

(1)

wherein $R^3$ is a hydrogen atom, a lower alkyl group or a lower alkoxy group, $R^4$ is a hydrogen atom, an acyl group, or a lower alkyl group, $R^5$ is a hydrogen atom or an optionally substituted lower alkyl group, $R^6$ is a hydrogen atom or a lower alkyl group, $R^7$ is a hydrogen atom, a lower alkyl group or a lower alkoxy group, Z is a sulfur atom, an oxygen atom, or a carbon atom substituted with a lower alkyl group, m is 1 or 2, and X is an anion.

The lower alkyl in $R^3$, $R^4$, $R^5$, $R^6$ and $R^7$ means a straight or branched alkyl group of a carbon number of 1 to 6, and examples include methyl, ethyl, propyl, butyl, isobutyl, sec-butyl, tert-butyl, pentyl and hexyl groups. Inter alia, a methyl group and an ethyl group are preferable.

The lower alkoxy group in $R^3$ and $R^7$ means an alkoxy group of a carbon number of 1 to 6, and examples include methoxy, ethoxy, and propoxy groups. Inter alia, a methoxy group and an ethoxy group are preferable. $R^3$ and $R^7$ are preferably a hydrogen atom.

The acyl group in $R^4$ is preferably an acyl derivatized from aliphatic carboxylic acid, and examples include acetyl, propionyl and the like. Inter alia, an acetyl group is preferable.

The optionally substituted lower alkyl group in $R^5$ means a lower alkyl group optionally substituted with 1 to 3 hydroxy groups, halogen atoms (fluorine, chlorine, bromine or iodine atom) and the like. Inter alia, a methyl group and an ethyl group substituted with one hydroxy group are preferable.

The lower alkyl group in Z is preferably such that Z is a sulfur atom.

Examples of the anion in X— include a halogen ion (fluorine, chlorine, bromine or iodine ion), a halogenated boron ion ($BF_4$—, $BCl_4$—, $BBr_4$— etc.), a phosphorus compound ion, a halogen oxygen acid ion, a fluorosulfate ion, a methylsulfate ion, a tetraphenylboron compound ion having a halogen or an alkyl group having a halogen as a substituent on an aromatic ring, and the like. Inter alia, a bromine ion or $BF_4$— is preferable.

As a specific example of the dye of the formula (1), the following dye A, dye B and dye C are preferable.

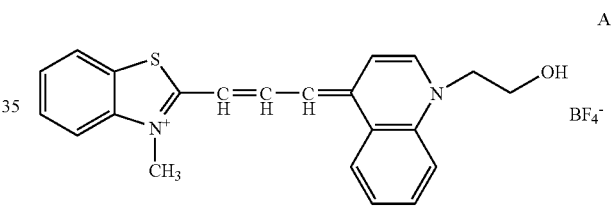

A

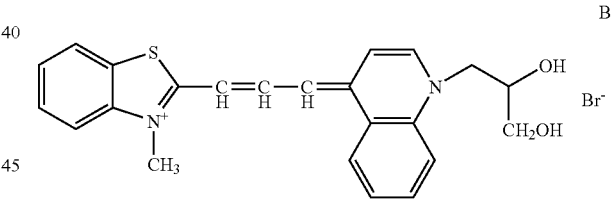

B

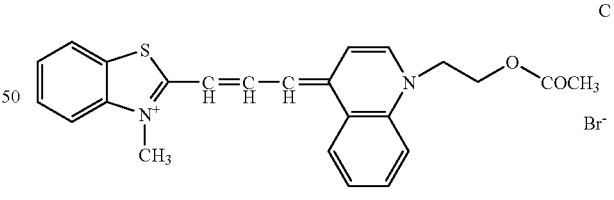

C

A dye concentration can be appropriately determined depending on a dye to be used. A concentration in a reagent is preferably 0.01 to 500 ppm, more preferably 0.1 to 200 ppm.

A cell membrane is damaged with the aforementioned surfactant, and a part in a cell is discharged to the outside of a cell, thereby, cell constriction occurs, or cell constriction occurs due to a change in the surface state of a cell membrane, but it is preferable that a solubilizer for sufficiently constricting a damaged cell is contained in order to render a hemocyte other than leukocyte, particularly, erythrocyte a ghost population which does not provide useful scattered light information and fluorescent information.

As the solubilizer, specifically, one or more selected from a sarcosine derivative represented by the following (2) or a salt thereof:

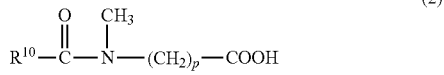

(wherein $R^{10}$ is an alkyl group of a carbon number of 10 to 22, and p is an integer of 1 to 5)
a cholic acid derivative represented by the following (3) formula;

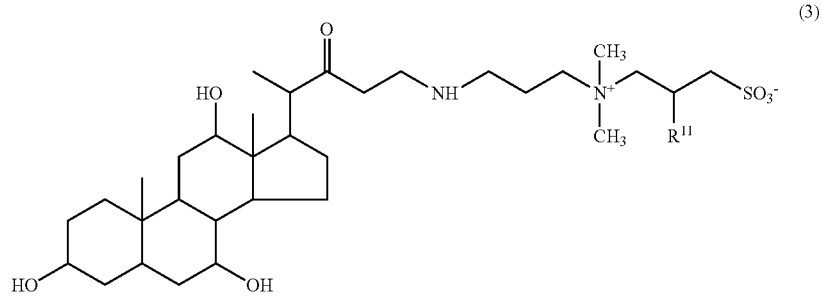

(wherein $R^{11}$ is a hydrogen atom or a hydroxy group) and methylglucan amide represented by the following (4) formula;

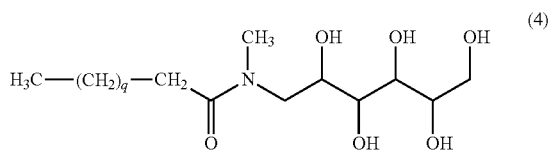

(wherein q is 5 to 7)
can be used.

Examples of the alkyl group of a carbon number of 10 to include decyl, dodecyl, tetradecyl, oleyl and the like.

Specific examples include sodium N-lauroylsarcosinate, lauroylmethyl β-alanine sodium, lauroylsarcosine, CHAPS (3-[3-cholamidopripyl]dimethylammonio)-1-propane sulfonate), CHAPSO (3-[3-cholamidoproypl]dimethylammonio)-2-hydroxy-1-propane sulfonate), MEGA8 (octanoyl-N-methylglucamide), MEGA9 (nonanoyl-N-methylglucamide), MEGA10 (decanoyl-N-methylglucamide) and the like.

It is preferable that a concentration of the solubilizer is 0.2 to 2.0 g/l in a sarcosinic acid derivative or a salt thereof, 0.1 to 0.5 g/l in a cholic acid derivative, and 1.0 to 8.0 g/l in methylglucaneamide.

As the solubilizer, in addition to the aforementioned solubilizers, n-octyl β-glucoside, sucrose monocaprate, N-formylmethylleucylalanine and the like may be used, and are preferably used at a concentration of 0.01 to 50.0 g/l.

Further more, it is preferable that a pH adjusting agent and a buffer for adjusting a pH of a reagent are contained and, furthermore, if necessary, it is preferable that an osmotic pressure adjusting agent is contained.

As the buffer, a Good buffer such as HEPES and the like, and a phosphate buffer are used. As the pH adjusting agent, sodium hydroxide is used. As the osmotic pressure adjusting agent, a sugar, an amino acid, an organic solvent, and sodium chloride are used. As the sugar, glucose, xylitol, mannitol, arabinose, and ribitol can be used. As the amino acid, alanine, proline, glycine, and valine can be used. As the organic solvent, ethylene glycol, and glycerin can be used. A concentration of the osmotic pressure adjusting agent in a reagent is appropriately adjusted by a molecular weight and, for example, in the case of use of xylitol, the concentration is preferably 10 to 75 g/l, in the case of use of glycerin, the concentration is preferably 5 to 45 g/l and, in the case of use of glycine, the concentration is preferably 5 to 45 g/l.

In the treating reagent having the aforementioned composition, it is preferable that a pH is 5.0 to 9.0, and an osmotic pressure is 150 to 600 mOsm/kg.

The treating reagent may be a one-pack reagent containing a surfactant, a dye, and other component, or a staining solution containing a fluorescent dye, and a solution (hemolyzing agent) containing the aforementioned surfactant may be accommodated in separated containers to obtain a reagent kit containing them. In this case, in order to enhance storage stability of a dye, it is preferable to use a water-soluble organic solvent such as ethylene glycol and the like as a solvent for a fluorescent dye.

[Preparation of Measuring Sample]

By mixing a solution containing the treatment reagent and a hematological sample, a measuring sample can be prepared. When the reagent kit is used, first, a solution (hemolyzing agent) containing a surfactant and a hematological sample may be mixed and, then, a staining solution may be mixed to obtain a measuring sample.

In mixing of a hematological sample and a treating reagent, it is preferable that a ratio of sample: treating reagent is 1:10 to 1:1000, and a reaction temperature is 20 to 40° C., and a reaction time is 3 seconds to 5 minutes, more preferably 4 seconds to 1 minute.

In the thus prepared measuring sample, erythrocyte and mature leukocyte are constricted to a small size. Particularly, since erythrocyte has no nucleus, hemolysis and cell constriction due to cell membrane damage progress, and since staining with a fluorescent dye is not performed, any of forward scattered light, side scattered light and fluorescent light is decreased, and this can be handled as a ghost population.

On the other hand, when a sample and a reagent are reacted for a predetermined time, mature leukocyte is constricted due to cell membrane damage, but since a nucleus is not substantially constricted, mature leukocyte does not become smaller as compared with erythrocyte. Furthermore, since a fluorescent dye can permeate through a damaged membrane, a nucleus is stained.

Since immature leukocyte has resistance to a hemolyzing agent as compared with mature leukocyte and erythrocyte, damage of a cell membrane needs a time. Therefore, cell constriction does not sufficiently occur within a predetermined reaction time, and since a fluorescent dye can not permeate through, a nucleus is hardly stained.

Regarding individual platelet cells, membrane damage with a treating reagent needs a time like immature leukocyte, and a dye does not penetrate into a platelet to stain platelet itself, but in the case of platelet aggregation body, a dye is physically adsorbed on a surrounding of an aggregate body, and the body is stained.

[Obtaining of Scattered Light Information and Fluorescent Information]

The prepared measuring sample is measured with a flowcytometer to obtain scattered light information and fluorescent information of a cell and platelet contained in a sample.

It is preferable that obtaining of information is performed by introducing a measuring sample into a flow cell of a flowcytometer, and irradiating a sample flowing in the flow cell with excitation light which can excite the fluorescent dye. Thereby, scattered light information and fluorescent information emitted from a cell passing through a flow cell can be obtained.

Irradiation light includes light having a wavelength which can excite a fluorescent dye used. Depending on a wavelength of light of a light source which is mounted on a flowcytometer used, a fluorescent dye which can be excited by the light may be selected.

As scattered light information, two kinds of scattered lights having different angles are obtained. Specifically, a combination of forward scattered light and side scattered light is preferably used.

Herein, forward scattered light is thought to be information reflecting a size of a cell. That is, when a cell is large, forward scattered light is great. Side scattered light is scattered light having an angle which is different by 80 to 100 degree, preferably 85 to 95 degree relative to forward scattered light. From side scattered light, cell internal information, particularly, information of a nucleus can be obtained. When a granule is contained, or a shape of a nucleus is irregular, side scattered light tends to increase.

In a predetermined reaction time, since a fluorescent dye hardly penetrates into the interior of platelet, platelet itself is hardly stained. However, since a fluorescent coloring matter binds to a surrounding of a platelet aggregation body, or a part in which platelets are adhered, in a measuring sample, as an aggregate body grows larger, a fluorescent intensity is increased. On the other hand, when platelet aggregation is small, and an aggregate body is small, since a side scattered light intensity is reduced, and a fluorescent dye to be adhered is reduced, a fluorescent intensity is consequently reduced.

[Specification of Cell Group and Counting of Myeloblast]

Using the obtained scattered light information and fluorescent information, an objective cell group is specified, and myeloblast is counted. The measuring method of the present invention can be classified into the following first measuring method to fourth measuring method from a viewpoint of a specification step. This will be explained sequentially below.

(1) First Measuring Method

In the first measuring method, a first cell group containing myeloblast is specified based on the obtained first scattered light information and second scattered light information (first specification step), a second cell group containing myeloblast is specified based on the obtained first scattered light information and the fluorescent information (second specification step), and a cell belonging to both of the first and second cell groups is counted as myeloblast. As an order of the first specification step and the second specification step, any of them may be performed first.

(1-1) First Cell Group

A first cell group is specified based on the obtained two kinds of scattered light information, preferably a forward scattered light intensity and a side scattered light intensity. It is preferable that a first cell group is specified by setting a region thought that myeloblast appears therein, in a scattergram using these two kinds of scattered light information as two axes (first scattergram). In addition, since an extent of staining and a size of myeloblast are different depending on a specimen, it is preferable that a region in which a first cell group appears, is set every specimen.

As the specific method of setting a region in which a first cell group appears, first, when a cell population is perceived at a position thought that myeloblast appears in a scattergram using two kinds of scattered light information as two axes, a center of this population is specified. From a center of a cell population of myeloblast to a part in which a cell of a myeloblast cell population appears until other cell population appearance region, can be determined as a boundary of a first cell group appearance region. Similarly, when a cell population is perceived at a position thought that other cell population (immature granulocyte, granulocyte, lymphocyte, monocyte) appears therein, a center of each population is specified and, at the same time, its appearance region is specified. These regions may be set in advance from data accumulated concerning various sizes of myeloblast, depending on a dye used, and a concentration.

When a region thought that each cell appears therein is set in a scattergram using a forward scattered light intensity (first scattered light information) in an ordinate, and a side scattered light intensity (second scattered light information) in an abscissa as two axes, the measuring sample used in the present invention generally becomes the state in FIG. 1. In FIG. 1, "Blast" is a myeloblast appearance region, "IG" is a immature granulocyte appearance region, "Gran" is a granulocyte appearance region, "Ly" is a lymphocyte appearance region, and "Mo" is a monocyte appearance region.

Since myeloblast is weak in a side scattered light intensity, it appears in a region on a relatively left side in a scattergram. On the other hand, since granulocyte, and immature granulocyte appear on a right side where side scattered light is relatively great, due to irregularity of a form of their nucleus, these populations appear in a region remote from a myeloblast appearance region. Therefore, as an appearance region of a first cell group, a region indicated with a chain line, surrounding a Blast part may be set.

Since platelet aggregation is versatile in an aggregation manner, a side scattered light intensity is from small to large, and since a size of an aggregate body is versatile as a few to a few tens, a forward scattered light intensity is from small to large. In this respect, since there is correlation between a size and irregularity of an aggregate body, in a scattergram shown in FIG. 1, the aggregate body appears in a region from left lower to right upper (region surrounded with dotted line), and is not overlapped with a region of Blast (first cell group appearance region).

According to FIG. 1, a first cell group is discriminated from platelet aggregation and other hemocyte component, and it is also thought that a first cell group can be counted as myeloblast. However, depending on a sample, lymphocyte having a great size is contained in some cases, and a part of a lymphocyte appearance region is overlapped with a first cell group appearance region, though it is a rare case.

(1-2) Second Cell Group

A second cell group is specified based on the obtained first scattered light information and fluorescent information, preferably forward scattered light information and fluorescent information. A second cell group is a cell population contained in a region thought that myeloblast appears in a scattergram (second scatter gram) using a forward scattered light intensity and a fluorescent intensity as two axes.

Since myeloblast and immature granulocyte do not substantially undergo membrane damage with a treating reagent within a predetermined reaction time, a nucleus is not stained, and they appear in a left region where a fluorescent intensity is low. Therefore, in a region thought that myeloblast appears therein, immature leukocyte also appears in some cases. On the other hand, since granulocyte, lymphocyte and monocyte undergo membrane damage with a treating reagent in a prescribed reaction time and a nucleus is stained, they appear in a right region where a fluorescent intensity is high, and can be clearly discriminated from an immature leukocyte population which does not substantially undergo nucleus staining in a predetermined reaction time. That is, in an appearance region of immature leukocyte including myeloblast, mature leukocyte does not sufficiently appear.

Therefore, as a specific method of specifying a second cell group appearance region, first, when a cell population is perceived at a position thought that myeloblast appears in a scattergram, a center of this population is specified. From a center of a cell population of myeloblast, to a part where a cell of a myeloblast cell population appears, until an appearance region of a cell population of mature leukocyte, can be determined as a boundary of a second cell group appearance region. Similarly, when a cell population is perceived at a position thought that other cell population (immature granulocyte, granulocyte, lymphocyte, monocyte) appears therein, a center of each population is specified and, at the same time, its appearance region is specified. These regions may be set in advance from data accumulated concerning of various sizes of myeloblast, depending on a dye used, and a concentration.

Figure 2:
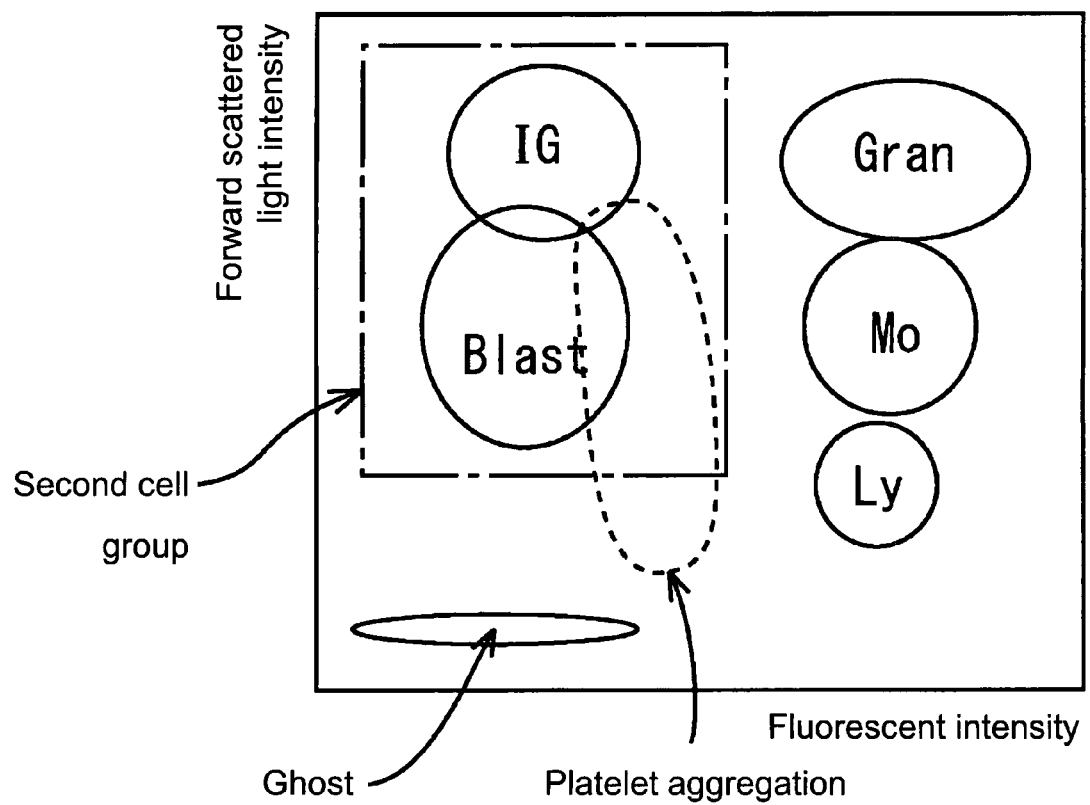
FIG. 2 is a scattergram for explaining a second cell group.

Specifically, as shown in FIG. 2, in a scattergram using a fluorescent intensity as an abscissa, and a forward scattered light intensity as an ordinate, a second cell group becomes a population contained in a region surrounded with a chain line, of a left region where a fluorescent intensity is low. In FIG. 2, "Blast" is a myeloblast appearance region, "IG" is a immature granulocyte appearance region, "Gran" is a granulocyte appearance region, "Ly" is a lymphocyte appearance region, and "Mo" is a monocyte appearance region.

Since platelet aggregation is stained to the extent where it is physically adsorbed, the platelet aggregation appears in a left region. In addition, since from a size smaller than that of myeloblast and a size larger than that of myeloblast can be present depending on an extent of aggregation, the platelet aggregation appears in a region extending longitudinally, from a small forward scattered light intensity to a large one, as shown in FIG. 2.

(1-3) Counting of Myeloblast

The above-specified cell contained in a first cell group and contained in a second cell group is counted as myeloblast.

Lymphocyte which may be contained in a first cell group is not contained in a second cell group. On the other hand, platelet aggregation, and immature leukocyte which may be contained in a second cell group are not contained in a first cell group. Therefore, a cell contained in a first cell group and contained in a second cell group does not include lymphocyte, platelet aggregation, and immature leukocyte, and it can be said that the cell substantially contains only myeloblast. Therefore, by counting a cell contained in a first cell group and contained in a second cell group as myeloblast, myeloblast can be precisely counted.

Alternatively, a cell contained in the first cell group and the second cell group may be discriminated by a scattergram (third scattergram) using fluorescent information and second scattered light information as two axes. A cell appearing in this third scattergram is substantially a population of only myeloblast.

Figure 3:
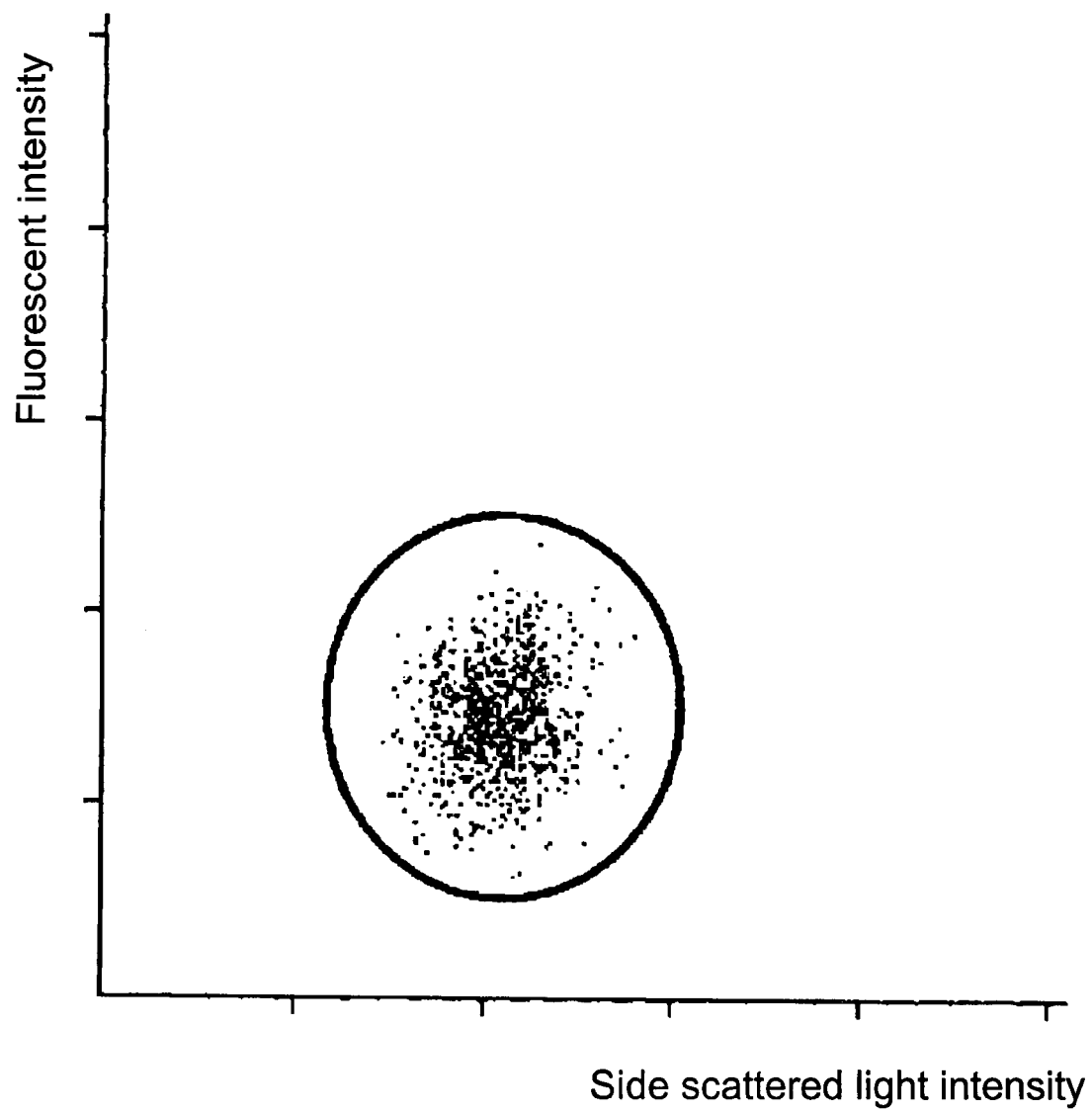
FIG. 3 is a scattergram for explaining a cell contained in a first cell group and contained in a second cell group.

First scattered light information is preferably a forward scattered light intensity, and second scattered light information is preferably a side scattered light intensity. When a cell contained in a first cell group and contained in a second cell group is discriminated by a scattergram (third scatter gram) using a fluorescent intensity and a side scattered light intensity as two axes, for example, a scattergram as shown in FIG. 3 is obtained. Since in this scattergram, a cell contained in a first cell group and contained in a second cell group, that is, substantially only myeloblast appears, a cell which appears here may be counted as myeloblast.

(2) Second Measuring Method

Although, in the first measuring method and the second measuring method, the first specification step and the second specification step were separately performed, to specify a first cell group and a second cell group, respectively, a first cell group (or a second cell group) may be specified first and, then, a second cell group (or a first cell group) may be specified among the first specified first cell group (or second cell group).

That is, in the second measuring method, a second cell group containing myeloblast is specified based on the obtained first scattered light information and fluorescent information (second specification step), then, based on first scattered light information and the second light information of the specified second cell group, a first cell group is specified among the second cell group (when a second measuring method is particularly referred, this specification step is referred to as "first' specification step", and a first cell group specified by the first' specified step is referred to as "first' cell group"), and this first' cell group is counted as myeloblast. Alternatively, a first cell group containing myeloblast is specified based on the obtained first scattered light information and second scattered light information (first specification step), then, a second cell group is specified among the first cell group based on first scattered light information and fluorescent information of the specified first cell group (when a second measuring method is particularly referred, this specification step is referred to as "second' specification step", and a second cell group specified by a second' specification step is referred to as "second' cell group"), and this second' cell group is counted as myeloblast.

A first specification step and a first cell group specified therein, and a second specification step and a second cell group specified therein are specified based on scattered light information and fluorescent information obtained in each obtaining step, and a specific procedure thereof is the same as that of the first measuring method, therefore, explanation is omitted.

(2-1) Specification of Second' Cell Group and Counting of Myeloblast

A second' specification step specifies a population containing myeloblast (specification of second' cell population) among the first cell group based on first scattered light information (preferably, forward scattered light intensity) and fluorescent information (preferably, fluorescent intensity) of the first specified first cell group. The thus specified second' cell group corresponds to a cell contained in a first cell group and contained in a second cell group in the first measuring method and the second measuring method.

Specification of a second' cell population is specifically performed as follows.

First, a scattergram (first scattergram) using first scattered light information and second scattered light information as axes is produced, and all components having a shape (cell, platelet etc.) are discriminate by this scattergram. A candidate region for myeloblast is set in this first scattergram, and a first cell group appearing in this region is specified. Then, a scattergram (second' scattergram) using first scattered light information and fluorescent information as two axes is produced, and only a first cell group is discriminated by this scattergram. A cell population contained in a region thought that myeloblast appears in a second' scattergram is a second' cell group. Since mature leukocyte and immature leukocyte are clearly discriminated in a second' scattergram using first scattered light information and fluorescent information as two axes, even when lymphocyte is contained in a first cell group, lymphocyte is not contained in a second' cell group discriminated by a second' scattergram. That is, a second' cell group is a myeloblast population not substantially containing other component such as platelet aggregation, and lymphocyte. Therefore, a cell contained in a second' cell group may be counted as myeloblast.

(2-2) Specification of First' Cell Group and Counting of Myeloblast

A first' specification step first specifies a second cell group by a second specification step, and specifies a population containing myeloblast (specification of first' cell population) among the second cell group based on first scattered light information (preferably, forward scattered light intensity) and second scattered information (preferably, side scattered light intensity) of the specified second cell group. The thus specified first' cell group corresponds to a cell contained in a first cell group and contained in a second cell group in the first measuring method and the second measuring method.

Specification of the first' cell population is specifically performed as follows: First, a scattergram (second scatter gram) using the obtained first scattered light information (preferably, forward scattered light intensity) and fluorescent information (preferably, fluorescent intensity) as two axes is produced, and all components having a shape (cell, platelet etc.) are discriminated by this scattergram. In this second scattergram, a candidate region of a second cell group containing myeloblast is specified. Then, a scattergram (first' scatter gram) using first scattered light information and second scattered light information as two axes is produced, and only the above specified second cell group is discriminated by this scattergram. A cell population contained in a region thought that myeloblast appears in a first' scattergram is a first' cell group. Since immature leukocyte and platelet aggregation appear in a region which can be clearly discriminated from a region where myeloblast appears in a first' scattergram using first scattered light information and second scattered light information as two axes, a first' cell group does not substantially contain other component such as platelet aggregation, lymphocyte, and immature leukocyte. Therefore, a cell contained in a first' cell group may be counted as myeloblast.

(3) Third Measuring Method

In first and second measuring methods, upon specification of a first cell population (or a first' cell population) and a second cell population (or a second' cell population), in any specification step, after respective cell populations were separately specified based on two kinds of information, a cell population contained in a first cell population and contained in a second cell population was specified, and this was counted as myeloblast. However, in the method of measuring a hematological sample of the present invention, using the obtained first scattered light information, second scattered light information, and fluorescent information, a first cell population and a second cell population may be specified in a single step, a cell contained in both of a first cell population and a second cell population may be determined, and this may be counted as myeloblast.

That is, in the third measuring method, a first cell group containing myeloblast is specified based on the obtained first scattered light information and second scattered light information and, at the same time, a second cell group containing myeloblast is specified based on the obtained first scattered light information and fluorescent information, and a cell contained in a first cell group and contained in the second cell group is counted as myeloblast.

Specifically, a sample is discriminated by a three-dimensional scattergram using first scattered light information, second scattered light information, and fluorescent information as three axes, a first cell group containing myeloblast is specified based on first scattered light information (preferably, forward scattered light intensity) and second scattered light information (preferably, side scattered light intensity) and, at the same time, a second cell group containing myeloblast is specified based on first scattered light information (preferably, forward scattered light intensity) and fluorescent information (preferably, fluorescent intensity). A method of specifying a first cell group and a method of specifying a second cell group thereupon can be performed as in the first measuring method.

In summary, in a three-dimensional scattergram, specification of a first cell group and specification of a second cell group can be performed simultaneously, and, further, a cell contained in a first cell group and contained in a second cell group can be specified. As described in the first measuring method, a cell contained in a first cell group and contained in a second cell group does not substantially contain other cell component such as platelet aggregation, lymphocyte and the like. Therefore, when a cell contained in a first cell group and contained in a second cell group is counted as myeloblast in a three-dimensional scattergram, myeloblast can be counted at a high precision.

(4) Fourth Measuring Method

A fourth measuring method is a method applied to the case where, as a cell group to be specified based on the obtained first scattered light information and fluorescent information, a third cell group containing a cell other than a ghost population (substantially total leukocyte, since in the measuring sample used in the present information, erythrocyte becomes a ghost population due to cell constriction) is specified in place of a second cell group containing myeloblast.

That is, in the fourth measuring method, a first cell group containing myeloblast is specified based on the obtained first scattered light information and second scattered light information (first specification step), a third cell group containing total leukocyte is specified based on the obtained first scattered light information and fluorescent information (third specification step), a fourth cell group not substantially containing at least mature leukocyte among the third cell group based on second scattered light information and fluorescent information of the third cell group (fourth specified step), and a cell contained in the first cell group and contained in the fourth cell group is counted.

Since the first specification step and the first cell group are the same as those of the first measuring method, explanation is omitted.

(4-1) Third Specification Step and Third Cell Group

Figure 4:
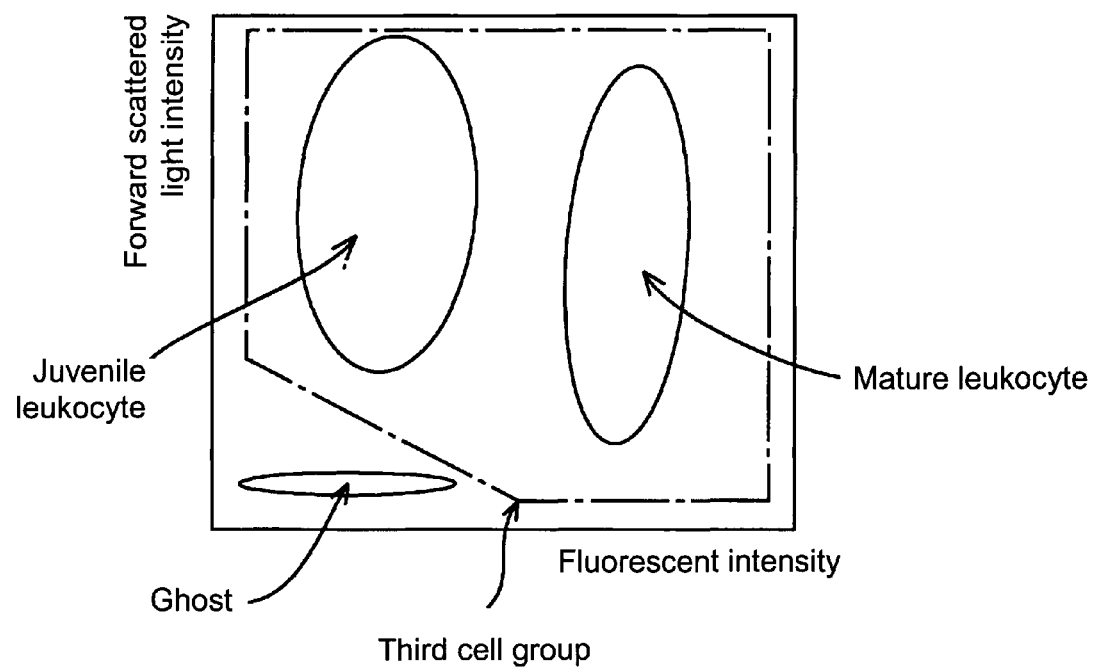
FIG. 4 is a scattergram for explaining a third cell group.

A third cell group is a cell population appearing in a region except for a region where an erythrocyte ghost population appears in a scattergram using a forward scattered light intensity and a fluorescent intensity as two axes, that is, a population of substantially total leukocyte. Specifically, a cell population appearing in a region surrounded with a chain line as shown in FIG. 4 when a scattergram using a fluorescent intensity as an abscissa, and a forward scattered light intensity as an ordinate is drawn, becomes a third cell group. In addition, a third cell group appearance region also contains platelet aggregation as shown in FIG. 2.

(4-2) Fourth Specification Step and Fourth Cell Group

A fourth cell group is specified based on second scattered light information and fluorescent information of a third cell group, preferably side scattered light information and fluorescent information. When a third cell group is discriminated by a scattergram using a fluorescent intensity and a side scattered light intensity as two axes, since a region where mature leukocyte appears, and a region where immature leukocyte appears are clearly discriminated, when a region thought that myeloblast is contained is specified in a scattergram using a fluorescent intensity and a side scattered light intensity as two axes, an appearance region of a cell population containing immature leukocyte, further, a population containing myeloblast can be specified. It is preferable that specification of a myeloblast candidate region herein is performed every specimen like specification of a first cell group or a second cell group. In addition, a region may be set in advance from data accumulated regarding various sizes of myeloblast and mature leukocyte, depending on a dye used, and a concentration.

Figure 5:
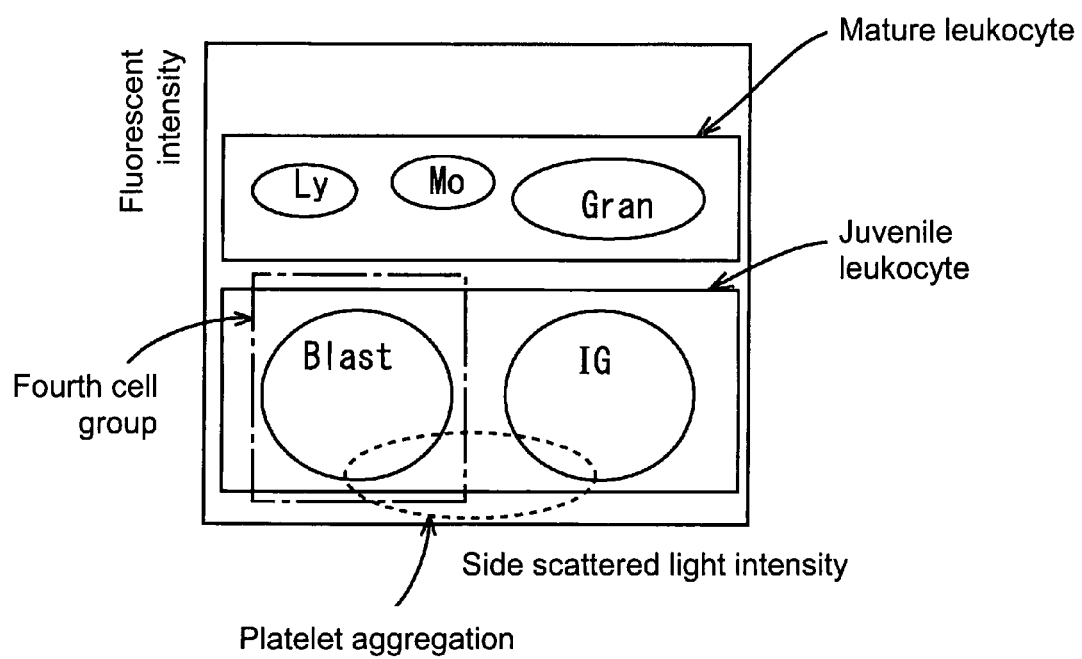
FIG. 5 is a scattergram for explaining a fourth cell group.

When a third cell group is discriminated by a scattergram using a side scattered light intensity as an abscissa, and a fluorescent intensity as an ordinate, as shown in FIG. 5, mature leukocyte (lymphocyte, monocyte, and granulocyte) appears upwardly due to a stained nucleus, and can be clearly discriminated from immature leukocyte whose nucleus is not substantially stained. Mature leukocyte appears as a lymphocyte population (Ly), a monocyte population (Mo) and a granulocyte population (Gran) in an order from a left side, depending on a nucleus form or the like. Platelet aggregation appears downwardly from a left side to a right side. Therefore, a cell population in a region surrounded with a chain line containing myeloblast, situated at a position of a relatively low to intermediate fluorescent intensity, in a left region where a side scattered light intensity is low, may be specified as a fourth cell group. Since myeloblast and immature granulocyte are different in a nuclear form and complexity, both can be discriminated by a magnitude of a side scattered light intensity, but when gating for clearly discriminating both of them is difficult, a cell population contained in a immature granulocyte appearance region, containing both of myeloblast and immature granulocyte may be adopted as a fourth cell group.

(4-3) Specification and Counting of Myeloblast

The above-specified cell contained in a first cell group and contained in a fourth cell group is counted. Since a first cell group does not contain platelet aggregation, and a fourth cell group does not contain mature leukocyte, a cell contained in a first cell group and contained in a fourth cell group is a population of myeloblast or immature leukocyte, which does not substantially contain platelet aggregation, and mature leukocyte. That is, even when lymphocyte is contained in a first cell group, since lymphocyte is excluded from a cell contained in a first cell group and contained in a fourth cell group, myeloblast or immature leukocyte can be substantially counted at a high precision.

[Discrimination Method]

A method for discriminating myeloblast and platelet aggregation contained in a hematological sample of the present invention is a method for discriminating a cell population containing myeloblast, and platelet aggregation in the measuring method of the present invention, by a step of a sample treatment step; a step of obtaining forward scattered light information and side scattered light information produced by irradiating the treated sample with light; and a step of specifying a first cell group containing myeloblast based on the forward scattered light information and the side scattered light information.

As described above, when a region thought that myeloblast appears therein is specified in a scattergram using forward scattered light information and side scattered light information as two axes, since the region is clearly discriminated from a region thought that platelet aggregation appears therein, myeloblast and platelet aggregation contained in a hematological sample can be discriminated.

[Apparatus for Measuring Hematological Sample]

The measuring apparatus of the present invention comprises a sample treatment part for giving damage to a cell membrane of erythrocyte and mature leukocyte contained in a hematological sample, constricting a hemocyte in which a cell membrane is damaged, and dyeing this with a fluorescent dye which can stain a nucleic acid; an obtainer for obtaining first scattered light information generated by irradiating the treated sample with excitation light of the fluorescent dye, second scattered light information based on scattered light having a different angle from that of first scattered light, and fluorescent information; a first classifier for specifying a first cell group containing myeloblast based on the first scattered light information and the second scattered light information; a second classifier for specifying a second cell group containing myeloblast based on the first scattered light information and the fluorescent information; and a calculator for counting a cell belonging to both of the first and second cell groups as myeloblast.

Figure 6:
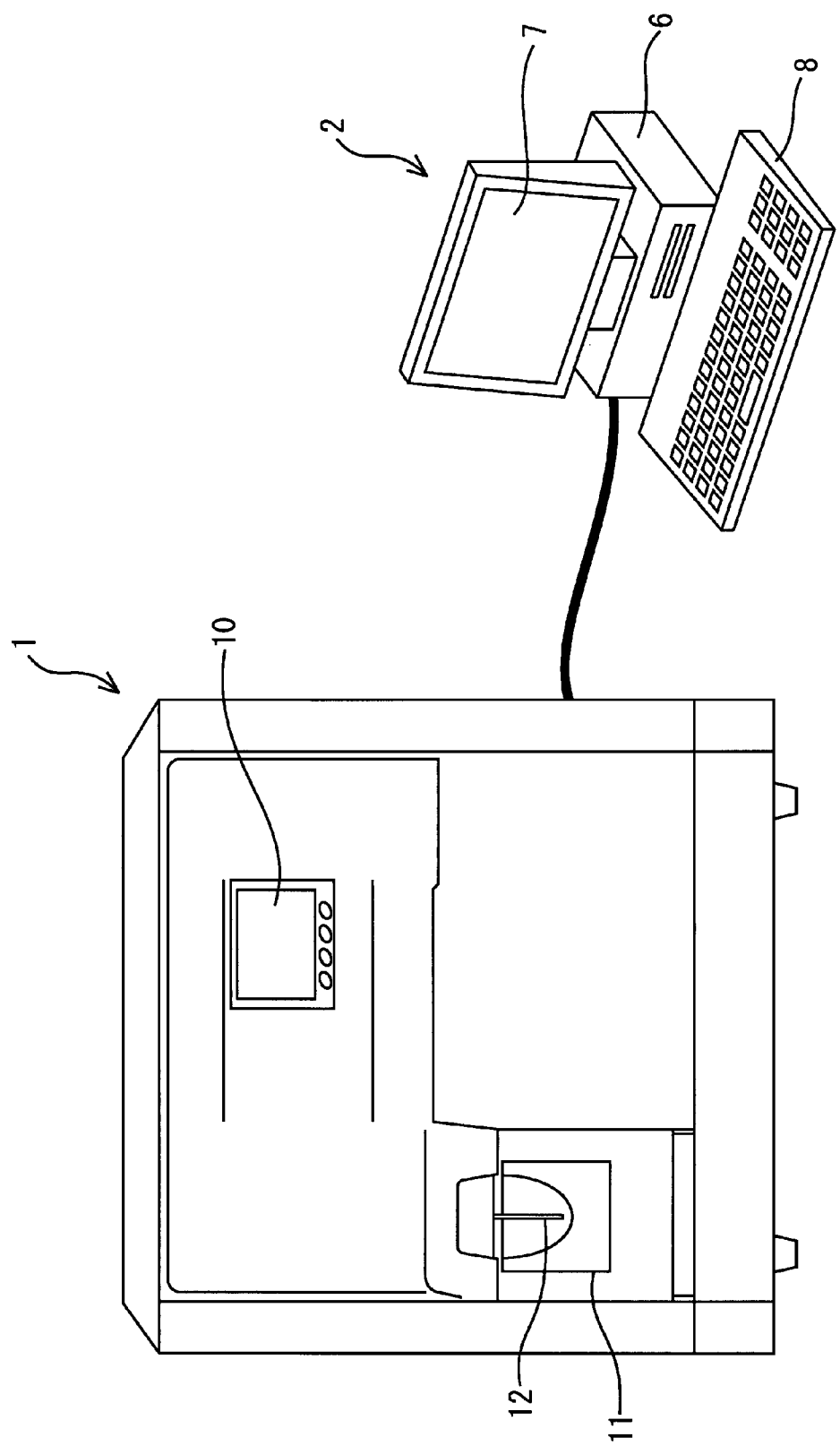
FIG. 6 is a view showing one example of appearance of the measuring apparatus of the present invention.

The measuring apparatus of the present invention has, as its appearance, for example, appearance shown in FIG. 6. The apparatus shown in FIG. 6 has a measuring part 1, an analyzing part 2, and a signal cable 3 connecting the analyzing part 2 and the measuring part 1. The measuring part 1 contains the a sample treatment part and the an obtainer of the apparatus of the present invention, and the analyzing part 2 contains the a first classifier, the a second classifier, and the a calculator of the present invention.

Figure 7:
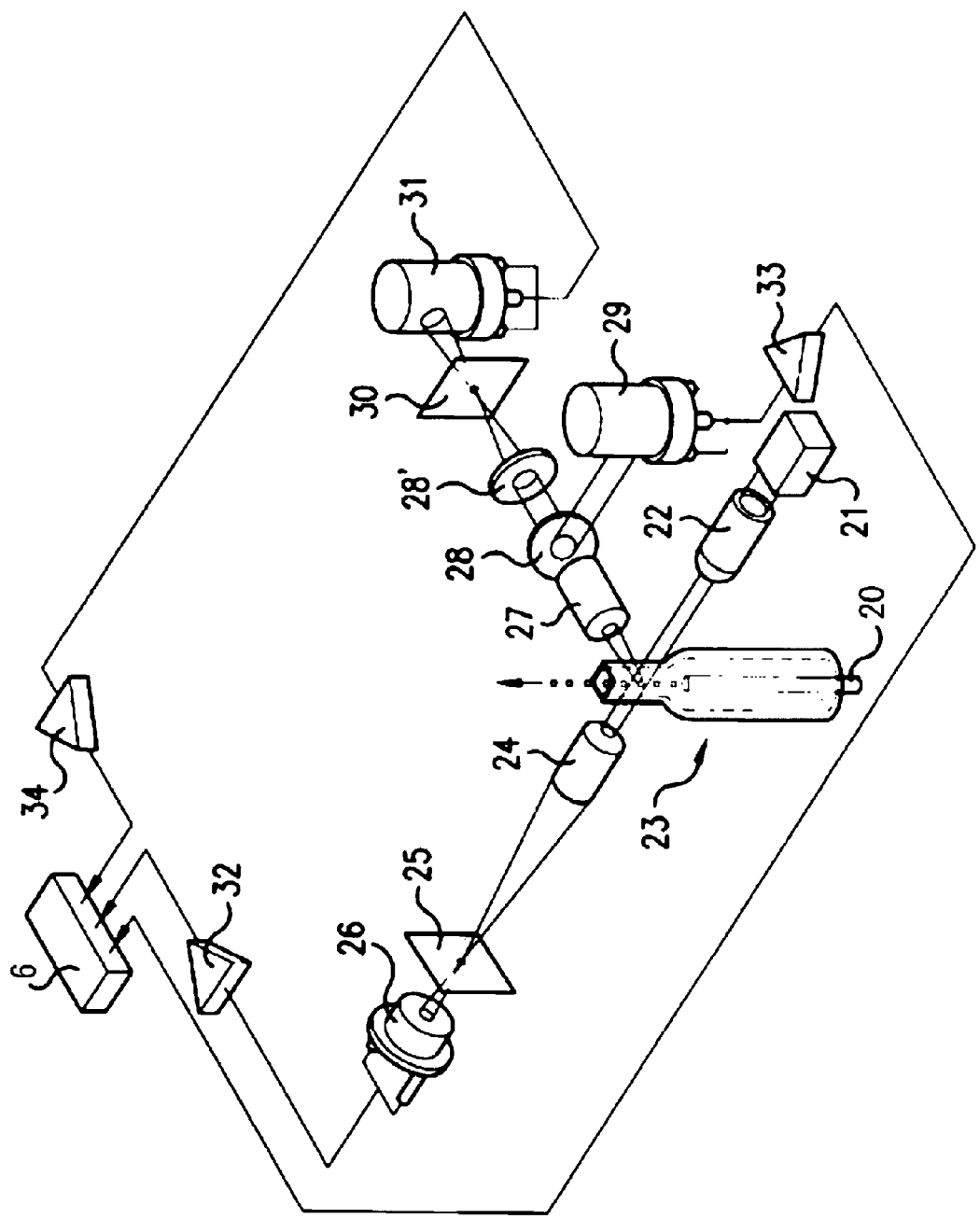
FIG. 7 is a view showing one example of a flowcytometer used in the measuring apparatus of the present invention.

The measuring part 1 is provided with a liquid crystal touch panel 10 for performing various setting inputs by an operator, and a start switch 11 for initiating measurement action, and a probe 12 for sucking a specimen. In addition, in the interior of the measuring part 1, a flowcytometer as shown in FIG. 7 is mounted. The analyzing part 2 is provided with a control part 6 for processing of information sent from the measuring part 1 and for controlling action of the measuring part 1, an output part 7 which is a display part for displaying various measurement results, and a keyboard 8 for inputting specimen information by an operator.

Then, the flowcytometer shown in FIG. 7 will be explained. A beam emitted from a light source (e.g. red semiconductor laser: wavelength 633 nm) 21 irradiates an orifice part of a sheath flow cell 23 via a collimating lens 22. Forward scattered light radiated from a hemocyte which is discharged from a nozzle 20 and passes through an orifice part is introduced into a forward scattered light detector (photodiode) 26 via a condensing lens 24 and a pinhole plate 25. On the other hand, side scattered light radiated from a hemocyte passing through an orifice part is introduced into a side scattered light detector (photomultiplier tube) 29 via a condensing lens 27 and a dichroic mirror 28. In addition, side fluorescent light radiated from a hemocyte passing through an orifice part is introduced into a side fluorescent light detector (photomultiplier tube) 31 via a condensing lens 27, a dichroic mirror 28, a filter 28' and a pinhole plate 30. A forward scattered light signal outputted from the forward scattered light detector 26, a side scattered light signal outputted from the side scattered light detector 29, and a side fluorescent signal outputted from the side fluorescent light detector 31 are amplified with amplifiers 32, 33, 34, respectively, and are inputted into the control part 6.

The light source 21 irradiates an orifice part of a flow cell into which the prepared measuring sample has been introduced, with light which can excite a dye used in treatment of a sample, and is selected depending on a fluorescent dye which stains a hemocyte in a sample. Therefore, depending on a kind of a fluorescent dye used, in addition to the red semiconductor laser, for example, an argon laser, a He—Ne laser, and a blue semiconductor laser may be used.

Figure 8:
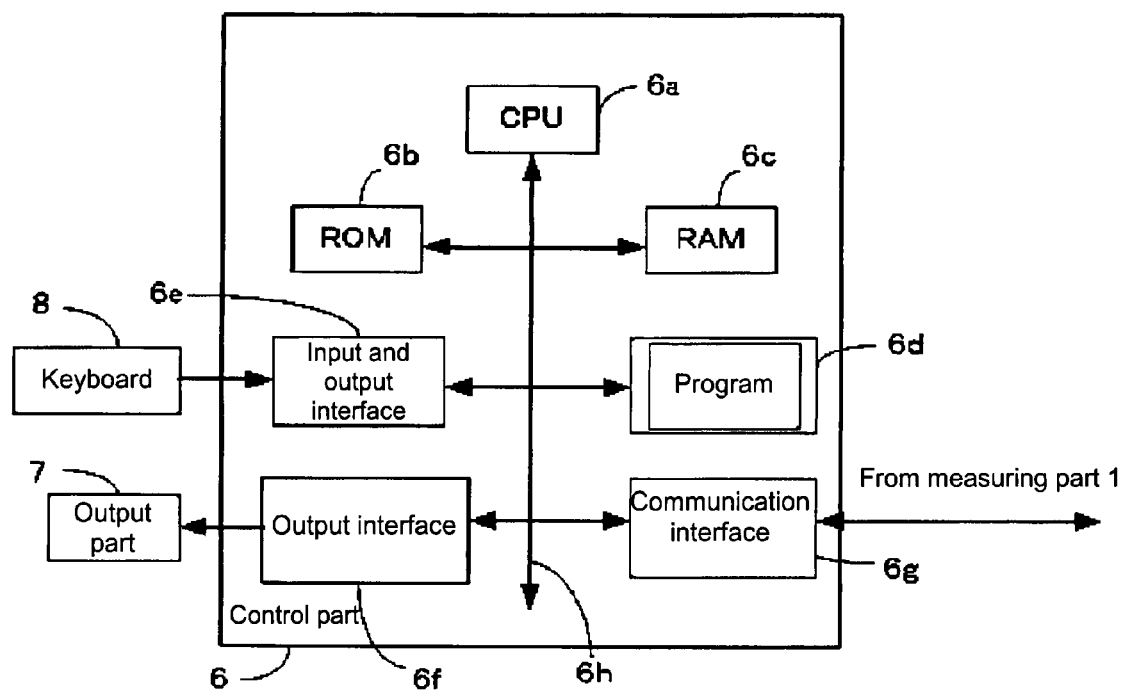
FIG. 8 is a block view showing one example of a construction of a control part used in the measuring apparatus of the present invention.

FIG. 8 is a block view showing a construction of the control part 6. This control part 6 is composed mainly of CPU6$a$, ROM6$b$, RAM6$c$, a hard disc 6$d$, an input and output interface 6$e$, an image outputting interface 6$f$, and a communication interface 6$g$, and the CPU6$a$, the ROM6$b$, the RAM6$c$, the hard disc 6$d$, the input and output interface 6$e$, the output interface 6$f$, and the communication interface 6$g$ are connected with a bus 6$h$ so that data can be communicated.

CPU6$a$ can execute a computer program stored in ROM6$b$ and a hard disc 6$d$, and a computer program read out into RAM6$c$. Therefore, the measuring part 1 specifically executes operation processing of a set program, specifies a cell group such as a first cell group and a second cell group and, further, counts myeloblast, based on a forward scattered light signal, a side scattered light signal, and a fluorescent signal, which are inputted from a flowcytometer.

ROM6$b$ stores a computer program to be executed by CPU6$a$, and data used for executing the computer program. RAM6$c$ is used in reading out of computer programs stored in ROM6$b$ and a hard disc 6$d$, and a working region of CPU6$a$ when a computer program is executed. The hard disc 6$d$ stores a computer program to be executed by CPU6$a$, and data used in executing the computer program. This computer program plays the function of analyzing optical information, and outputting the analysis result.

A keyboard 8 is connected to an input and output interface 6$e$. The keyboard 8 which is an input part is provided for operation on an output screen. An output interface 6$f$ is connected to an output part 7 consisted of a liquid crystal display. The output part 7 is provided for outputting and displaying the analysis result obtained in the controlling part 6. A communication interface 6$g$ is connected to the measuring part 1, and plays the function for receiving optical information.

Figure 9:
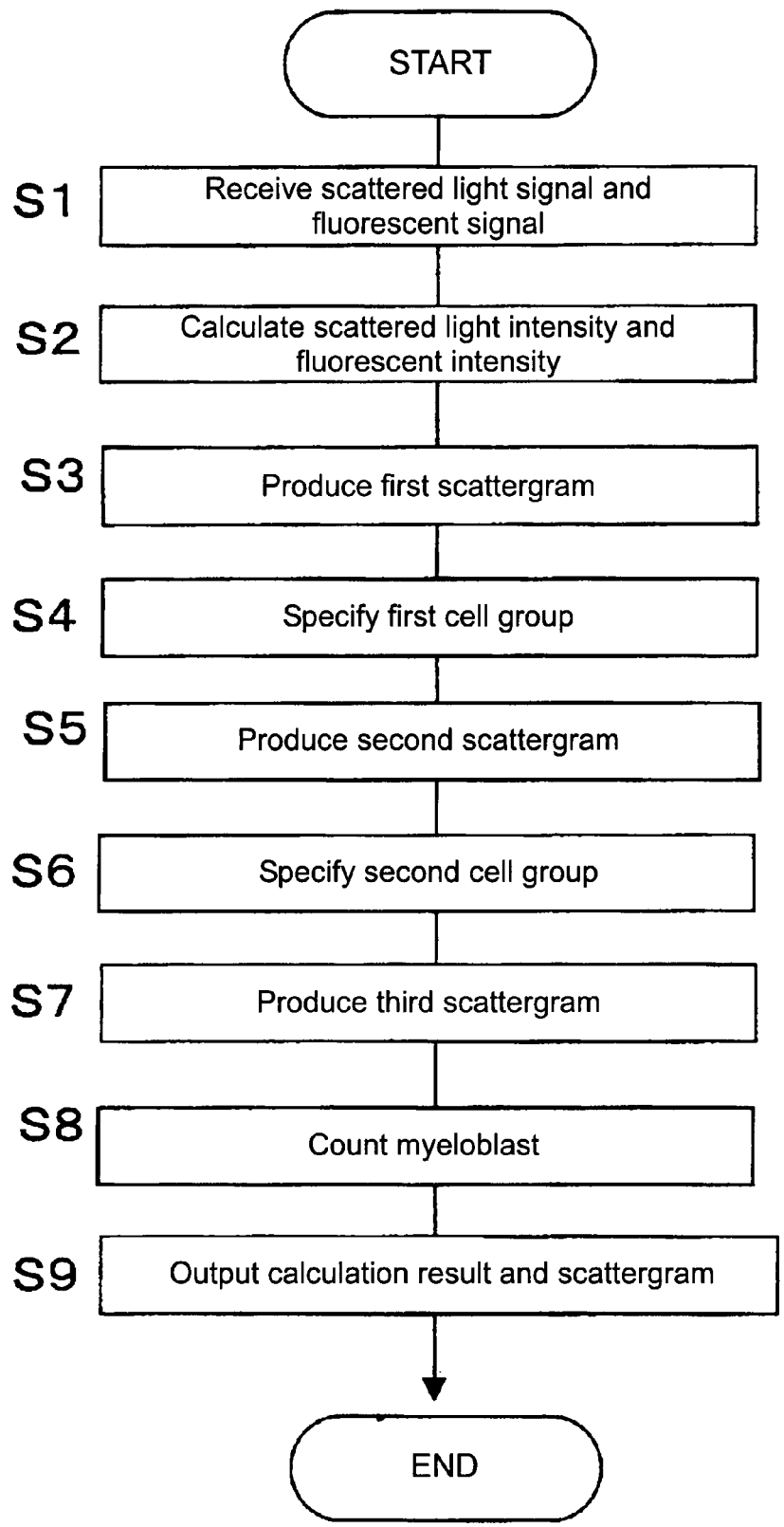
FIG. 9 is a flow chart showing one example of information processing adopted in the measuring apparatus of the present invention.

Then, an embodiment of information processing in the control part 6 will be explained. FIG. 9 is a flow chart showing information processing corresponding to the first measuring method of the present invention. When the control part 6 adopts the second measuring method, first, the part receives a forward scattered light signal, a side scattered light signal and a fluorescent signal detected in the measuring part 1, via a signal cable 3 (step S1). The control part 6 analyzes these signals, and calculates respective signal intensities (step S2). Then, using a forward scattered light intensity and a side scattered light intensity of a formed element (cell, platelet etc.) in a sample, a first scattergram using a forward scattered light intensity and a side scattered light intensity as two axes is produces (step S3). In a first scattergram, a myeloblast candidate region thought that myeloblast appears therein, is set, and a first cell group contained in this region is specified (step S4). Separately, using a forward scattered light intensity and a fluorescent intensity of a formed element in a sample, a second scattergram using a forward scattered light intensity and a fluorescent intensity as two axes is produced (step S5). In a second scattergram, a myeloblast candidate region thought that myeloblast appears therein, is set, and a second cell group contained in this region is specified (step S6). Then, using a fluorescent intensity and a side scattered light intensity of a cell contained in a first cell group and contained in a second cell group, a third scattergram using a fluorescent intensity and a side scattered light intensity as two axes is produced (step S7). A cell appearing in this third scattergram (cell contained in first cell group and contained in second cell group) is counted as myeloblast (step S8), and this counting result and the third scattergram are outputted in an output part 7 (step S9).

Figure 10:
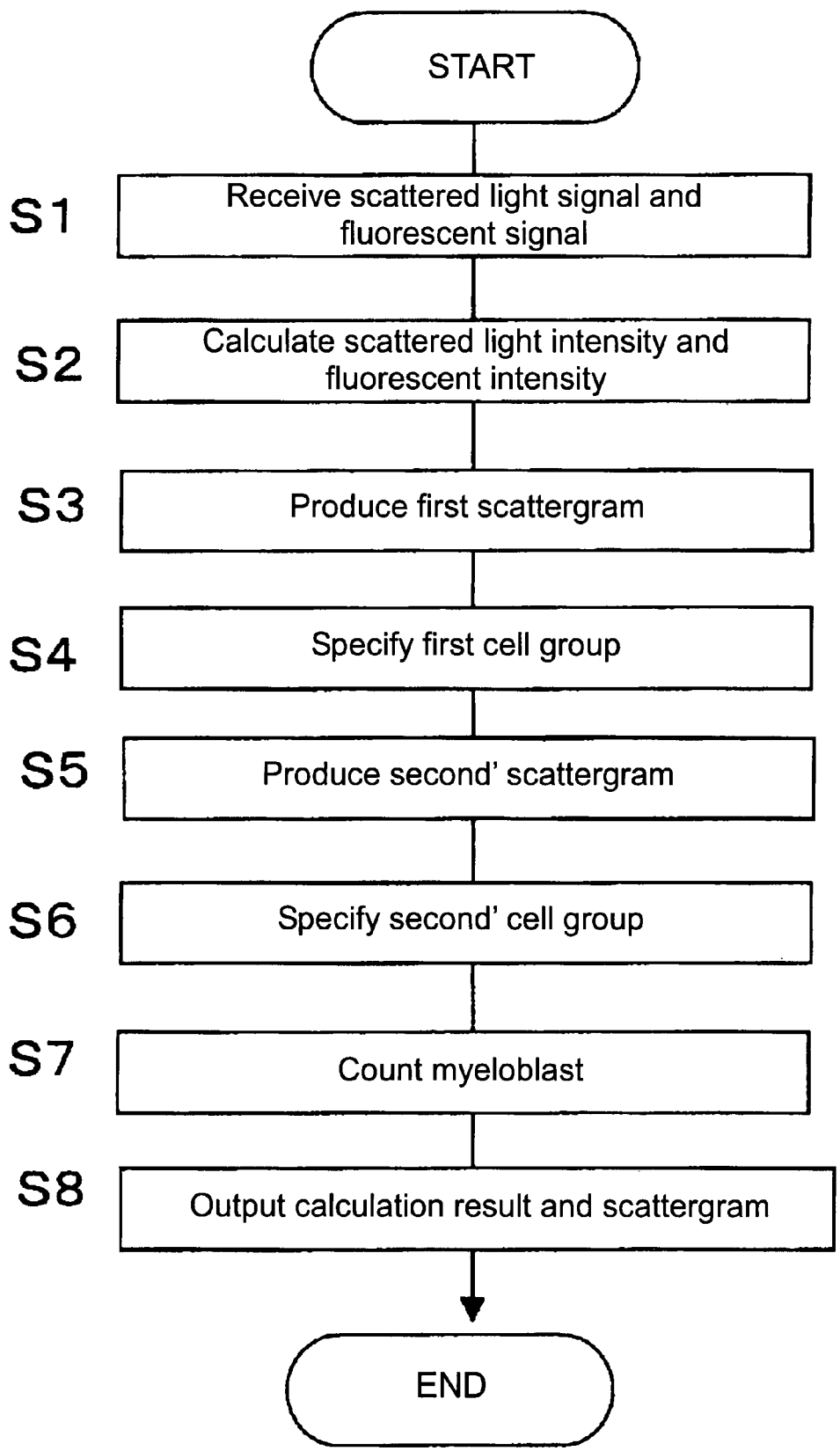
FIG. 10 is a flow chart showing other example of information processing adopted in the measuring apparatus of the present invention.

FIG. 10 is a flow chart showing information processing corresponding to a method of first specifying a first cell group among the second measuring method of the present invention. When the control part 6 adopts such the second measuring method, first, a forward scattered light signal, a side scattered light signal and a fluorescent signal detected in the measuring part 1 are received via a signal cable 3 (step S1). The control part 6 analyzes these signals, and calculates respective signal intensities (step S2). Then, using a forward scattered light intensity and a side scattered light intensity of a formed element (cell, platelet etc.) in a sample, a first scattergram using a forward scattered light intensity and a side scattered light intensity as two axes is produced (step S3). In the first scattergram, a myeloblast candidate region thought that myeloblast appears therein, is set, and a first cell group contained in this region is specified (step S4). Separately, using a forward scattered light intensity and a fluorescent intensity of a first cell group, a scattergram (second' scattergram) using a forward scattered light intensity and a fluorescent intensity as two axes is produced (step S5). In the second' scattergram, a myeloblast candidate region thought that myeloblast appears therein, is set, and a second' cell group contained in this candidate region is specified (step S6). This second' cell group is counted as myeloblast (step S7), and this counting result and the second' scattergram are outputted in an output part 7 (step S8).

Figure 11:
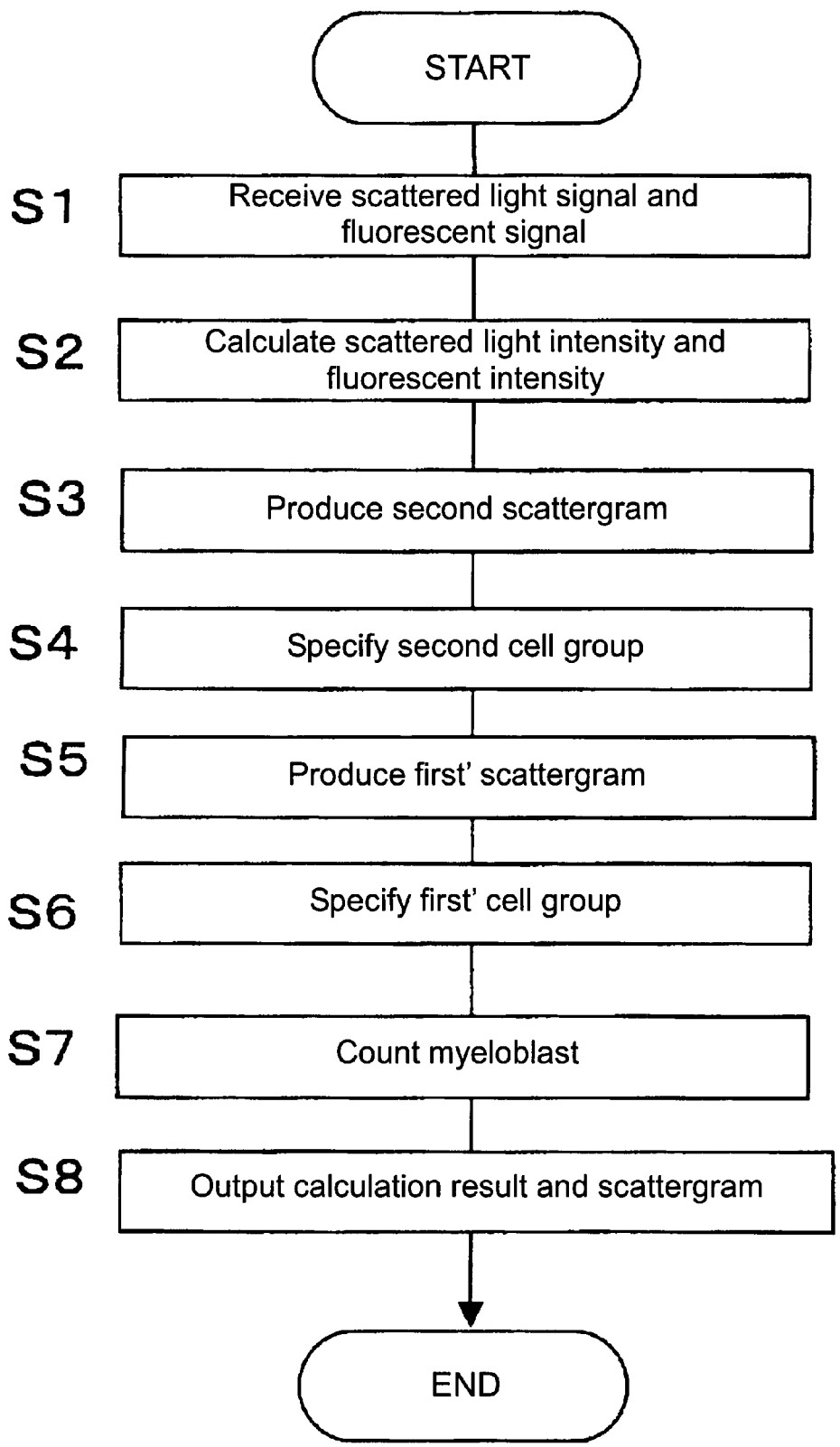
FIG. 11 is a flow chart showing other example of information processing adopted in the measuring apparatus of the present invention.

FIG. 11 is a flow chart showing information processing corresponding to a method of first specifying a second cell group among the second measuring method of the present invention. When the control part 6 adopts such the second measuring method, first, a forward scattered light signal, a side scattered light signal and a fluorescent signal detected in the measuring part 1 are received via a signal cable 3 (step S1). The control part 6 analyzes these signals, and calculates respective signal intensities (step S2). Then, using a forward scattered light intensity and a fluorescent signal of a formed element (cell, platelet etc.) in a sample, a second scattergram using a forward scattered light intensity and a fluorescent intensity as two axes is produced (step S3). In the second scattergram, a myeloblast candidate region thought that myeloblast appears therein, is set, and a second cell group contained in this region is specified (step S4). Then, using a forward scattered light intensity and a side scattered light intensity of a second cell group, a scattergram (first' scattergram) using a forward scattered light intensity and a side scattered light intensity as two axes is produced (step S5). In the first' scattergram, a myeloblast candidate region thought that myeloblast appears therein, is set, and a first' cell group contained in this candidate region is specified (step S6). This first' cell group is counted as myeloblast (step S7), and this counting result and the first' scattergram are outputted in an output part 7 (step S8).

Figure 12:
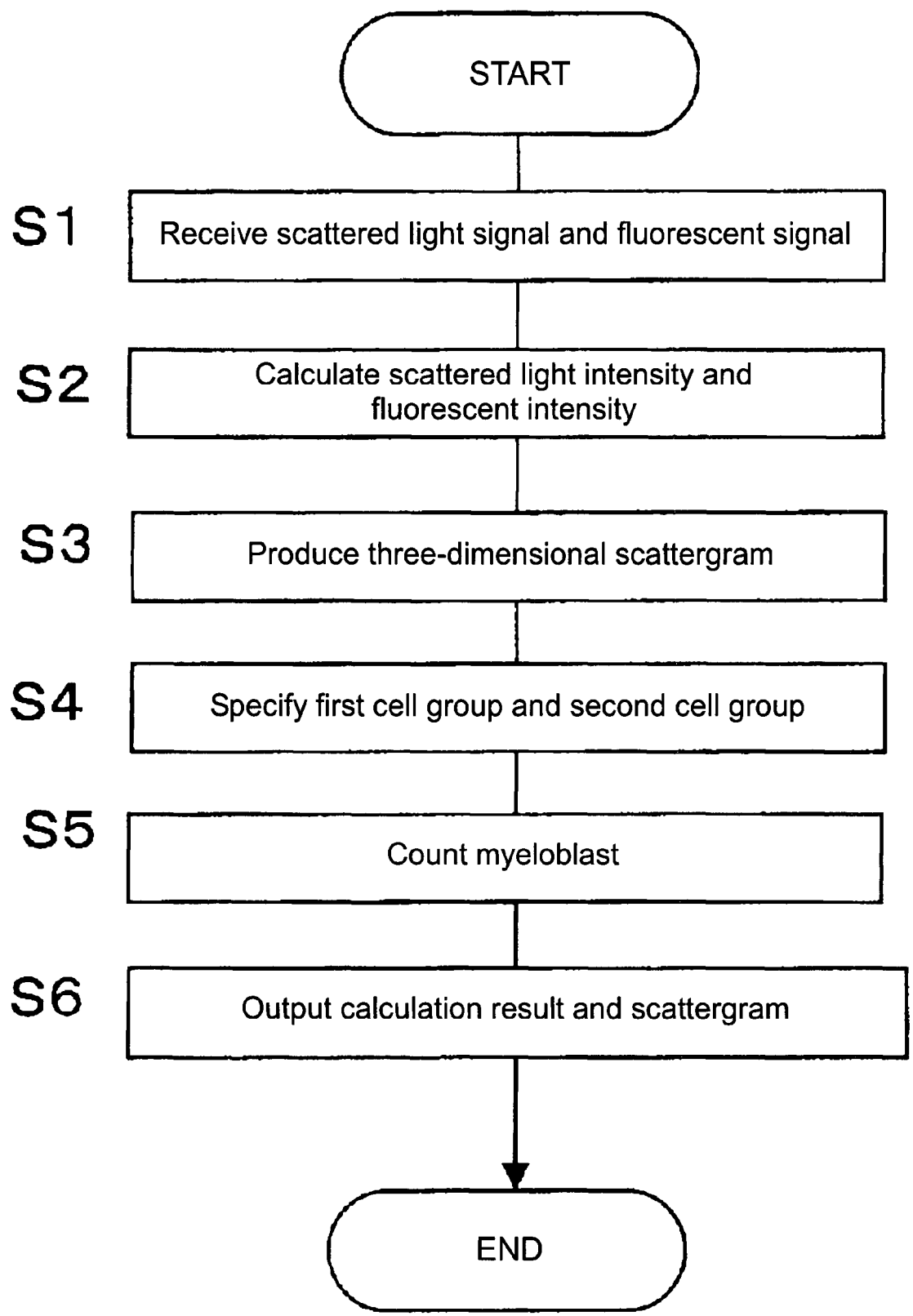
FIG. 12 is a flow chart showing other example of information processing adopted in the measuring apparatus of the present invention.

FIG. 12 is a flow chart showing information processing corresponding to the third measuring method of the present invention. When the control part 6 adopts such the third measuring method, first, a forward scattered light signal, a side scattered light signal and a fluorescent signal detected in the measuring part 1 are received via a signal cable 3 (step S1). The control part 6 analyzes these signals, and calculates respective signal intensities (step S2). Then, a three-dimensional scattergram using a forward scattered light intensity, a side scattered light intensity and a fluorescent intensity of a formed element (cell, platelet etc.) in a sample is produced (step S3).

In this three-dimensional scattergram, a first cell group based on a forward scattered light intensity and a side scattered light intensity, and a second cell group based on a forward scattered light intensity and a fluorescent intensity are specified (step S4). A myeloblast region where a cell contained in a first cell group and contained in a second cell group appears, is set in this three-dimensional scattergram, and a cell appearing in this region is counted as myeloblast (step S5). The result of counting of myeloblast, and the three-dimensional scattergram are outputted in an output part 7 (step S8).

In the apparatus of the aforementioned embodiment, the control part 6 outputs and displays the result of counting of myeloblast, and a scattergram used in counting on a display of an output part 7, but may output any of them. In addition, when a scattergram is outputted, not only a scattergram which is finally used in counting myeloblast, but also all of produced scattergrams may be outputted.

The measuring apparatuses of the aforementioned embodiments adopts the first to third measuring methods of the present invention, but when a fourth measuring method is adopted, it is preferable that the apparatus further comprises third specification means for specifying a fourth cell group not containing at least mature leukocyte based on the obtained fluorescent information and second scattered light information, and the a calculator is means for counting, as myeloblast, a cell belonging to both of the first and second cell groups and contained in a cell group specified by third specifying means.

Regarding an apparatus adopting the fourth measuring method, specifically, only information processing in the control part 6 of the aforementioned embodiment may be changed, provided that in a second classifier, as a second cell group specified based on first scattered light information and fluorescent information, a population of total leukocyte containing myeloblast (corresponding to third cell group) is specified and, in third specification means, in order to specify a fourth cell group, a scattergram using second scattered light information (side scattered light intensity) and fluorescent information (fluorescent intensity) as two axes is produced. And, a cell contained in a first cell group, contained in a second cell group (herein, substantially corresponding to a third cell group), and contained in a fourth cell group is counted, and the calculation result is outputted in an output part 7.

The "counting result of myeloblast" referred in the above embodiment includes the number of myeloblast in a sample, the number of myeloblast per unit volume (concentration), and a ratio of myeloblast relative to total leukocyte, and the control part 6 can output at least one of them.

EXAMPLE

Hematological Sample

As a hematological sample, a sample containing a large amount of myeloblast (sample a), and a sample containing myeloblast and immature leukocyte (sample b) were used. Samples a and b contain platelet aggregation.

[Preparation of Measuring Sample]

(1) Measuring Sample Using Treating Reagent A (A-1) Hemolyzing Agent

A hemolyzing agent of the following composition containing the following components was prepared.

| Glycine | 19.5 g/l |
|---|---|
| Polyoxyethylene(16)oleyl ether | 25.0 g/l |
| Sodium N-lauroylsarcosinate | 0.75 g/l |
| HEPES | 10 mM |
| Purified water | 1 l |
| Sodium hydroxide | amount to adjust a pH at 7.0 |

(A-2) Staining Solution

A fluorescent dye A represented by the following formula was dissolved in ethylene glycol.

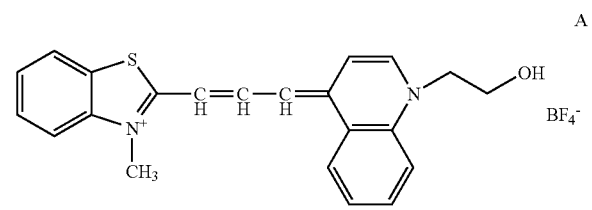

A

The hemolyzing agent and the hematological sample were mixed, and this was mixed with the staining solution so that a final concentration of a fluorescent dye became 20 ppm, to prepare a measuring sample.

(2) Measuring Sample Using Treating Reagent B

According to the same matter as that of the treating reagent A except that a hemolyzing agent having the following composition was used, a measuring sample was prepared.

| Xylitol | 37.0 g/l |
|---|---|
| Polyoxyethylene(16)oleyl ether | 25.0 g/l |
| Sodium N-lauroylsarcosinate | 0.75 g/l |

| | |
|---|---|
| HEPES | 10 mM |
| Purified water | 11 |
| Sodium hydroxide | amount to adjust a pH at 7.0 |

Measurement

Example 1

The hematological sample a and the treating reagent B were mixed, and reacted at 33° C. for 5 seconds to prepare a measuring sample, which was introduced into a flow cell, and forward scattered light, side scattered light and fluorescent light were measured with a flowcytometer (light source: red semiconductor: wavelength: 633 nm). Measurement results are shown in a first scattergram (FIG. 13(a)) using a forward scattered light intensity and a side scattered light intensity as two axes, and a second scattergram (FIG. 13(b)) using a fluorescent intensity and a forward scattered light intensity as two axes.

In FIG. 13 (a), an appearance region of a first cell group is a region surrounded with a solid line. In FIG. 13 (b), an appearance region of a second cell group is a region surrounded with a solid line. In FIG. 13 (a), a cell population containing lymphocyte was spread and a part of thereof was overlapped with a first cell group.

Figure 14:
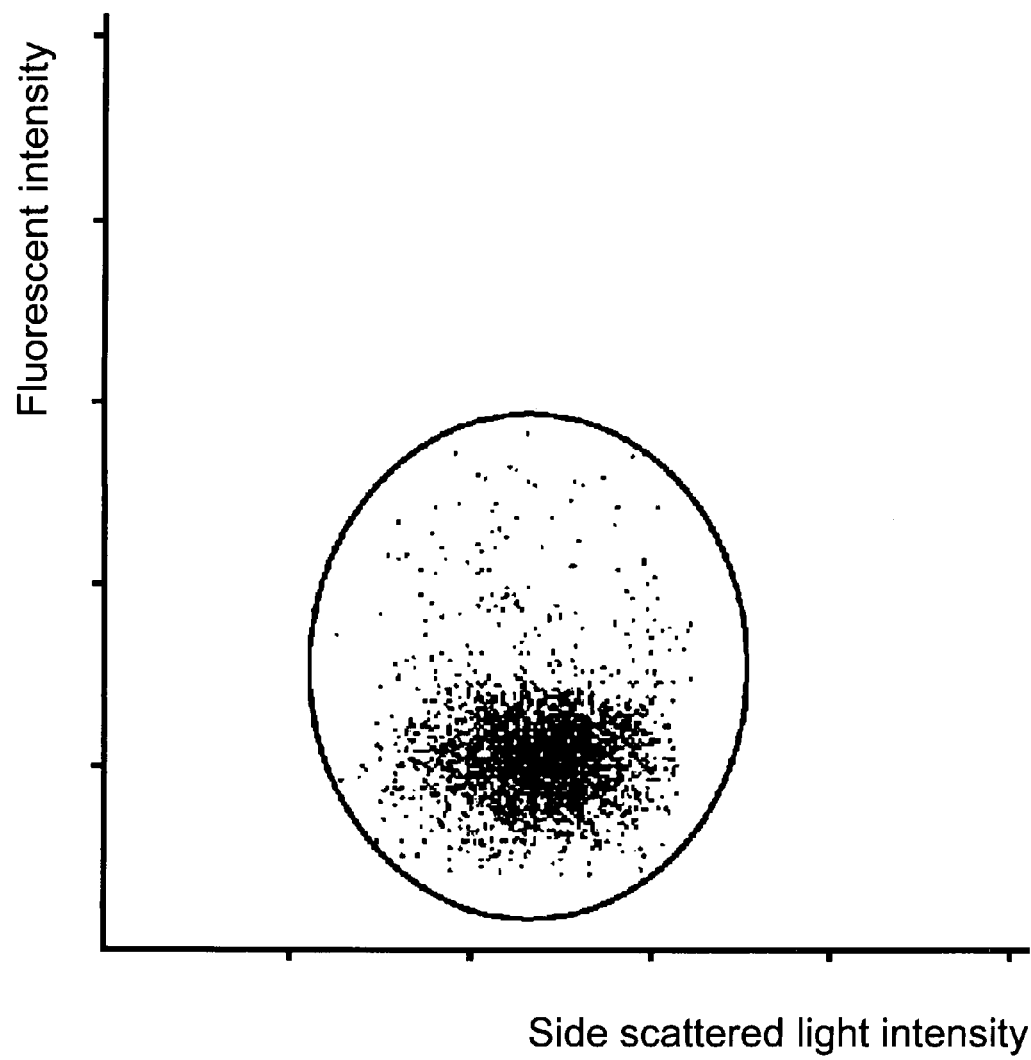
FIG. 14 is a third scattergram produced for a cell contained in both of a first cell group and a second cell group, regarding Example 1.

A cell population contained in both of a first cell group and a second cell group is shown in FIG. 14. FIG. 14 is a third scattergram using a side scattered light intensity and a fluorescent intensity as two axes, and a cell population contained in both of a first cell group and a second cell group appeared concentratedly in a part surrounded with a solid line.

The number of cells in a region surrounded with a solid line in FIG. 14 was counted, and a ratio relative to the number of total leukocyte was calculated, and was found to be 58.5%. On the other hand, the hematological sample a was observed with a microscope, and myeloblast was counted. A ratio of myeloblast relative to the number of total leukocyte in the field was obtained, and was found to be 42.0%.

Therefore, it was confirmed that, according to the measuring method of the present invention, myeloblast can be detected at the same extent of precision as that of microscope observation.

Example 2

A measuring sample prepared by treating the hematological sample b with the treating reagent A at 33° C. for 5 minutes was introduced into a flow cell, and forward scattered light, side scattered light, and fluorescent light were measured with a flowcytometer (light source: red semiconductor, wavelength: 633 nm). The measurement results are shown in a first scattergram (FIG. 15 (a)) using a forward scattered light intensity and a side scattered light intensity as two axes, and a second scattergram (FIG. 15(b)) using a fluorescent intensity and a forward scattered light intensity as two axes.

Figure 16:
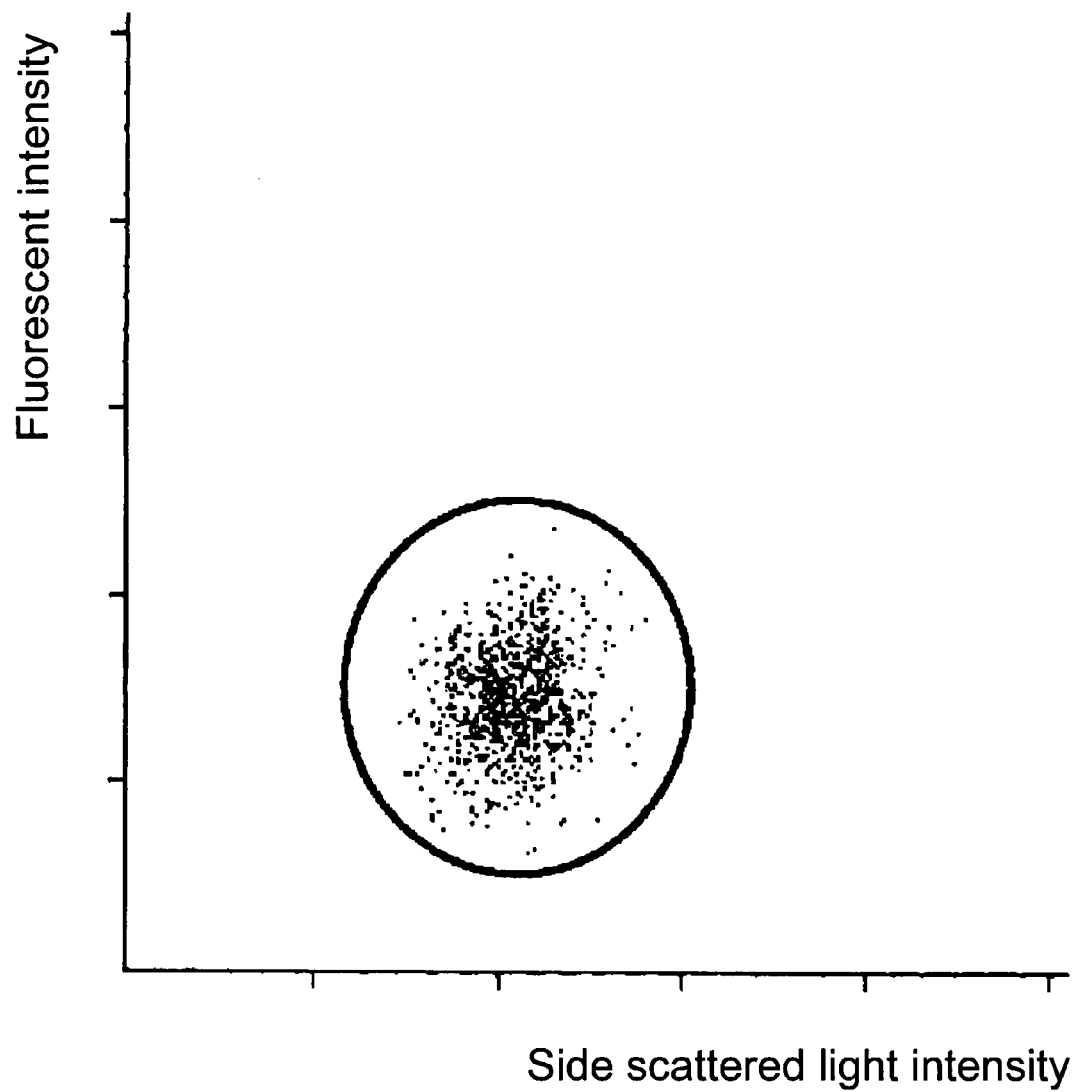
FIG. 16 is a third scattergram produced for a cell contained in both of a first cell group and a second group, regarding a measuring sample of Example 2.

In FIG. 15 (a), an appearance region of a first cell group is a region surrounded with a solid line. In FIG. 15 (b), an appearance region of a second cell group is a region surrounded with a solid line. A cell population contained in both of a first cell group and a second cell group is shown in FIG. 16. FIG. 16 is a third scattergram using a side scattered light intensity and a fluorescent intensity as two axes, and a cell population contained in both of a first cell group and a second cell group appeared concentratedly in a part surrounded with a solid line.

The number of cells in a region surrounded with a solid line in FIG. 16 was counted, and a ratio relative to the number of total leukocyte was calculated, and found to be 2.4%. On the other hand, the hematological sample a was observed with a microscope, and myeloblast was counted. A ratio of myeloblast relative to total leukocyte was 2.5%.

Therefore, it was confirmed that, according to the measuring method of the present invention, myeloblast can be detected at the same extent of precision as that of microscope observation and, particularly, myeloblast can be detected at a high precision, distinguishing also from immature granulocyte.

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is:

1. An apparatus for measuring a hematological sample, comprising:
   a sample treatment part for preparing a measurement sample by giving damage to a cell membrane of erythrocyte and mature leukocyte contained in the hematological sample, constricting the damaged erythrocyte, and staining the damaged mature leukocyte with a fluorescent dye for staining nucleic acid;
   an obtainer for obtaining first scattered light information generated by irradiating the measurement sample with light, second scattered light information based on scattered light having a different angle from that of first scattered light, and fluorescent information;
   a first classifier for specifying a first cell group containing myeloblast based on the first scattered light information and the second scattered light information;
   a second classifier for specifying a second cell group containing myeloblast based on the first scattered light information and the fluorescent information; and
   a calculator for calculating cells that belong to both of the first cell group and the second cell group as myeloblast.

2. The measuring apparatus according to claim 1, further comprising a scattergram preparer for preparing a first scattergram using the first scattered light information and the second scattered light information and a second scattergram using the first scattered light information and the fluorescent information; and
   wherein the first cell group is set in the first scattergram as a myeloblast appearance candidate region, and the second cell group is set in the second scattergram as a myeloblast appearance candidate region.

3. The measuring apparatus according to claim 2, further comprising a scattergram preparer for preparing a third scattergram including cells belonging to both of the first cell group and the second cell group by using the fluorescent information and the second scattered light information; and
   wherein the calculator calculates cells appearing in the third scattergram as myeloblast.

4. The measuring apparatus according to claim 1, wherein the second classifier specifies that part of the second cell group that also belongs to the first cell group, based on first scattered light information and fluorescent information of the first cell group.

5. The measuring apparatus according to claim 1, wherein the first classifier specifies that part of the first cell group that also belongs to the second cell group, based on first scattered light information and second scattered light information of the second cell group.

6. The measuring apparatus according to claim 1, wherein the first classifier and the second classifier are a single classifier for specifying the first cell group containing myeloblast based on the first scattered light information and the second scattered light information, and specifying the second cell group containing myeloblast based on the first scattered light information and the fluorescent information.

7. The measuring apparatus according to claim 1, wherein the first scattered light information is a forward scattered light intensity, the second scattered light information is a side scattered light intensity and the fluorescent information is a fluorescent intensity.

8. The measuring apparatus according to claim 1, wherein the sample treatment part mixes a surfactant for giving damage to the cell membrane of erythrocyte and mature leukocyte, and a solubilizer for constricting the damaged erythrocyte, the fluorescent dye, and the hematological sample.

9. The measuring apparatus according to claim 1, further comprising a scattergram preparer for preparing a scattergram using two information selected from the group consisting of the first scattered light information, the second scattered light information and the fluorescent information, and a display part for displaying more than one scattergram and a result of counting of myeloblast.

10. An apparatus for measuring a hematological sample, comprising:
 a sample treatment part for preparing a measurement sample by giving damage to a cell membrane of erythrocyte and mature leukocyte contained in the hematological sample, constricting the damaged erythrocyte, and staining the damaged mature leukocyte with a fluorescent dye for staining nucleic acid;
 an obtainer for obtaining first scattered light information generated by irradiating the measurement sample with light, second scattered light information based on scattered light having a different angle from that of first scattered light, and fluorescent information;
 a first classifier for specifying a first cell group containing myeloblast, based on the first scattered light information and the second scattered light information;
 a second classifier for specifying a cell population other than a ghost population as a second cell group, based on the first scattered light information and the fluorescent information;
 a third classifier for specifying a third cell group not substantially containing at least mature leukocyte among the third cell group, based on the second scattered light information and the fluorescent information; and
 a calculator for calculating cells that belong to both of the first cell group and the third cell group as myeloblast.

11. The measuring apparatus according to claim 10, wherein the first, second, and third classifier are a single classifier (1) for specifying the first cell group containing myeloblast based on the first scattered light information and the second scattered light information, (2) for specifying the second this cell group containing myeloblast based on the first scattered light information and the fluorescent information, and (3) for specifying the third cell group based on second scattered light information and fluorescent information.

12. The measuring apparatus according to claim 10, wherein the first scattered light information is a forward scattered light intensity, the second scattered light information is a side scattered light intensity, and the fluorescent information is a fluorescent intensity.

13. The measuring apparatus according to claim 10, wherein the sample treatment part mixes a surfactant for giving damage to the cell membrane of erythrocyte and mature leukocyte, a solubilizer for constricting the damaged erythrocyte, the fluorescent dye, and the hematological sample.

14. The measuring apparatus according to claim 10, further comprising a scattergram preparer for preparing a scattergram in which the cells contained in the first cell group and contained in the third cell group appear, and a display part for displaying more than one of the scattergrams and a result of counting of myeloblast.

15. A method of measuring a hematological sample, comprising steps of:
 preparing a measurement sample by giving damage to a cell membrane of erythrocyte and mature leukocyte contained in the hematological sample, constricting the damaged erythrocyte, and staining the damaged mature leukocyte with a fluorescent dye for staining nucleic acid;
 obtaining first scattered light information generated by irradiating the measurement sample with light, second scattered light information based on scattered light having a different angle from that of first scattered light, and fluorescent information;
 specifying a first cell group containing myeloblast, based on the first scattered light information and the second scattered light information;
 specifying a second cell group containing myeloblast, based on the first scattered light information and the fluorescent information; and
 counting cells that belong to both of the first cell group and the second cell group as myeloblast.

16. The measuring method according to claim 15, further comprising a step of preparing a scattergram including a cell belonging to both of the first and second cell groups by using the fluorescent information and the second scattered light information; and
 wherein the counting step is performed so as to count a cell appearing in the scattergram.

17. The method according to claim 15, wherein the second cell group specifying step is performed so as to specify the second cell group among the first cell group, based on the first scattered light information and the fluorescent information of the first cell group.

18. The method according to claim 15, wherein the first cell group specifying step is performed so as to specify the first cell group among the second cell group, based on the first scattered light information and the second scattered light information of the second cell group.

19. The method according to claim 15, further comprising a step of preparing a first scattergram using the first scattered light information and the second scattered light information and a second scattergram using the first scattered light information and the fluorescent information; and
 wherein the first cell group specifying step is performed so as to set a first myeloblast appearance candidate region in the first scattergram and specify a cell group appearing in first myeloblast appearance candidate region as the first cell group,
 and the second cell group specifying step is performed so as to set a second myeloblast appearance candidate region in the second scattergram and specify a cell group appearing in the second myeloblast appearance candidate region as the second cell group.

20. The method according to claim 15, wherein the first cell group specifying step and the second cell group specifying step is performed so as to specify the first cell group containing myeloblast based on the first scattered light information and the second scattered light information, and specify the second cell group containing myeloblast based on the first scattered light information and the fluorescent information as a single step.

* * * * *